US005874546A

United States Patent [19]
Nagata et al.

[11] Patent Number: 5,874,546
[45] Date of Patent: Feb. 23, 1999

[54] FAS ANTIGEN

[75] Inventors: Shigekazu Nagata, Suita; Naoto Itoh, Minoo; Shin Yonehara, Tokyo-to, all of Japan

[73] Assignee: Osaka Bioscience Institute, Osaka, Japan

[21] Appl. No.: 219,237

[22] Filed: Mar. 28, 1994

Related U.S. Application Data

[63] Continuation of Ser. No. 872,129, Apr. 22, 1992, abandoned.

[30] Foreign Application Priority Data

Apr. 26, 1991  [JP]  Japan .................................. 3-125234

[51] Int. Cl.$^6$ ....................... C07K 14/475; C07K 14/435
[52] U.S. Cl. ........................ 530/395; 530/350; 530/324; 530/325; 530/326; 530/327; 530/328; 530/329; 530/330; 530/331; 935/12; 935/34; 935/37; 935/38; 935/66; 935/69; 935/72; 435/69.3; 435/320.1
[58] Field of Search ................................ 435/69.3, 320.1; 935/12, 34, 37, 38, 66, 69, 72; 530/350, 395, 324–331

[56] References Cited

U.S. PATENT DOCUMENTS 4,879,213  11/1989  Fox et al. ...................................... 435/5

FOREIGN PATENT DOCUMENTS

| 0308265 A3 | 3/1989 | European Pat. Off. . |
| 0330191 | 8/1989 | European Pat. Off. . |
| WO8807549 | 10/1988 | WIPO . |
| WO9110448 | 7/1991 | WIPO . |

OTHER PUBLICATIONS

American Type Culture Collection (ATCC) Catalogue of Cell Lines and Hybridomas, Fifth Edition, pp. 245–246, 1985.

Burgess et al. The Journal of Cell Biology 111:2129–2138, Nov. 1990.
Lazar et al. Molecular and Cellular Biology 8(3):1247–1252, Mar. 1988.
Trauth et al. Science 245:301–305 1989.
Bonie et al. Science 247:1306–1310 1990.
Kumar et al. PNAS 87:1337–1341 1990.
"Vaccine Immunotherphy" S.J. Crya (Ed) published 1991 by Pergamon Pr See Chpt 17.
Kobayashi et al. PNAS 87:9620–24 1990 (Dec.).
Smith et al. Science 248:1019–23 May 1990.
Guo et al. Gene 29:1984 pp. 251–254.
In Glover et al. 1986. See Campo et al. pp. 213–214 IRL Press. Chapter 8.
Yonehara et al. J. Exp. Med. 169:1748–56 May 1989.
Mizushima et al., Nucleic Acids Research.
In Glover et al. 1986. See Gorman High Efficiency Gene Transfer into Mammalian Cells 143–164 IRL Press Chapter 6.
Langley et al. Gene 67:229–245 1988.
Journal of Biological Chemistry, vol. 267, No. 15, pp. 10709–10715 (May 25, 1992).
Cell, vol. 66, No. 2, pp. 233–244 (Jul. 26, 1991).
Immunobiology, vol. 181, No. 2–3, p. 127 (1990).
Science, vol. 245, No. 4915, pp. 301–305 (Jul. 21, 1989).

*Primary Examiner*—Anthony C. Caputa
*Attorney, Agent, or Firm*—Birch, Stewart, Kolasch & Birch, LLP

[57] ABSTRACT

DNAs coding for human cell surface antigen (Fas or Fas antigen), vectors for expressing for said DNAs and transformants transfected with said vector are provided. Fas is a polypeptide that exists in the surfaces of a variety of cells and is considered to be deeply concerned with the apoptosis of cells. The isolated Fas cDNA has an open reading frame that is capable of encoding a protein consisting of 335 amino acids. The mature Fas antigen is a protein consisting of 319 amino acids having a calculated molecular weight of about 36,000 and is constituted by an extracellular domain of 157 amino acids, a membrane-spanning domain of 17 amino acids, and a cytoplasmic domain of 145 amino acids.

9 Claims, 13 Drawing Sheets

Fig. 1A

```
GACGCTTCTG GGGAGTGAGG GAAGCGGTTT ACGAGTGACT TGGCTGGAGC CTCAGGGGCG GGCACTGGCA CGGAACACAC
CCTGAGGCCA GCCCTGGCTG CCCAGGCGGA GCTGCCCTCT TCTCCCGCGGG TTGGTGGACC CGCTCAGTAC GGAGTTGGGG
AAGCTCTTTC ACTTCGGAGG ATTGCTCAAC AACC                                              194

ATG CTG GGC ATC TGG ACC CTC CTA CCT CTG GTT CTT ACG TCT GTT GCT AGA TTA TCG TCC AAA AGT
Met Leu Gly Ile Trp Thr Leu Leu Pro Leu Val Leu Thr Ser Val Ala Arg Leu Ser Ser Lys Ser
            -10                                      -1  1

GTT AAT GCC CAA GTG ACT GAC ATC AAC TCC AAG GGA TTG GAA TTG AGG AAG ACT GTT ACT ACA GTT
Val Asn Ala Gln Val Thr Asp Ile Asn Ser Lys Gly Leu Glu Leu Arg Lys Thr Val Thr Thr Val
            10                                20

GAG ACT CAG AAC TTG GAA GGC CTG CAT GAT GGC GGT CTG CAA TTC TGC CAT AAG CCC TGT CCT CCA GGT
Glu Thr Gln Asn Leu Glu Gly Leu His Asp Gly Gly Leu Gln Phe Cys His Lys Pro Cys Pro Pro Gly
        30                               40                                       50

GAA AGG AAA GCT AGG GAC AAA GCC CAT TTT TCT TCC AAA TGC AGA CCA GAT GAA CCA TGC AGA TGT AGA TTG TGT GAT GAA GGA
Glu Arg Lys Ala Arg Asp Lys Ala His Phe Ser Ser Lys Cys Arg Pro Asp Glu Pro Cys Arg Leu Cys Asp Glu Gly
                                        60                                       70

AAG GAG TAC ACA GAC AAA GAT GAA ATA AAC TGC ACC CGG ACC CAG AAT ACC AAG TGC CGA TGT AAA CCA AAC
Lys Glu Tyr Thr Asp Lys Asp Glu Ile Asn Cys Thr Arg Thr Gln Asn Thr Lys Cys Arg Cys Lys Pro Asn
                                80                                              90

CAT GGC TTA GAA GTG GAG GTG CAA GTG CAA GTA TGT GAC CAC TGT GAC CCT TGC ACC AAA TGT GAA CAT GGA ATC ATC
His Gly Leu Glu Val Glu Val Cys Glu His Cys Asp Pro Cys Thr Lys Cys Glu His Gly Ile Ile
                            100                                         110

TTT TTT TGT AAC TCT ACT GTA TGT AAC TCT ACT GTA TGT
Phe Phe Cys Asn Ser Thr Val Cys Asn Ser Thr Val Cys
                    *120                                    130
```

Fig. 1B

```
AAG GAA TGC ACA CTC ACC AGC AAC ACC AAG TGC AAA GAG GAA GGA TCC AGA TCT AAC TTG GGG TGG
Lys Glu Cys Thr Leu Thr Ser Asn Thr Lys Cys Lys Glu Glu Gly Ser Arg Ser Asn Leu Gly Trp
140                         150                         160

CTT TGT CTT CTT TTG CCA ATT CCA CTA ATT GTT TGG GTG AAG AGA AAG GAA GTA CAG AAA ACA
Leu Cys Leu Leu Leu Pro Ile Pro Leu Ile Val Trp Val Lys Arg Lys Glu Val Gln Lys Thr
                170                         180

TGC AGA AAG CAC AGA AAG GAA CAA CAA GGT TCT CAT GAA TCT CCA ACC TTA AAT CCT GAA ACA GTG
Cys Arg Lys His Arg Lys Glu Asn Gln Gly Ser His Glu Ser Pro Thr Leu Asn Pro Glu Thr Val
                    190                         200

GCA ATA AAT TTA TCT GAT GTT AGT AAA TAT ATC ACC ACT ATT GCT GGA GTC ATG ACA CTA
Ala Ile Asn Leu Ser Asp Val Ser Lys Tyr Ile Thr Thr Ile Ala Gly Val Met Thr Leu
                        210                         220

AGT CAA GTT AAA GGC TTT GTT CGA AAG AAT GGT GTC AAT GAA GCC AAA ATA GAT GAG ATC AAG AAT
Ser Gln Val Lys Gly Phe Val Arg Lys Asn Gly Val Asn Glu Ala Lys Ile Asp Glu Ile Lys Asn
                230                         240

GAC AAT GTC CAA GAC ACA GCA GAA CAG AAA GTT CAA CTG CTT CGT AAT TGG CAT CAA CTT CAT GGA
Asp Asn Val Gln Asp Thr Ala Glu Gln Lys Val Gln Leu Leu Arg Asn Trp His Gln Leu His Gly
250                         260                         270

AAG AAA GAA GCG TAT GAC ACA TTG ATT AAA GAT CTC AAA AAA
Lys Lys Glu Ala Tyr Asp Thr Leu Ile Lys Asp Leu Lys Lys
                    280
```

Fig. 2A

```
                                                                              1150
GCC AAT CTT TGT ACT CTT GCA GAG AAA ATT CAG ACT ATC ATC CTC AAG GAC ATT ACT AGT GAC TCA
Ala Asn Leu Cys Thr Leu Ala Glu Lys Ile Gln Thr Ile Ile Leu Lys Asp Ile Thr Ser Asp Ser
                              290                             300

GAA AAT TCA AAC TTC AGA AAT GAA ATC CAA AGC TTG GTC TAG AGTGAAAAACAACAAATTCAGTTCTGA
Glu Asn Ser Asn Phe Arg Asn Glu Ile Gln Ser Leu Val End
310                 315                 320
                                                       1250                          1300
GTATATGCAATTAGTGTTTGAAAAGATTCTTAATAGCTGGCTGTAAATACTGCTTGGTTTTTTACTGGGTACATTTTATC

1350
ATTTATTAGCGCTGAAGAGCCAACACATATTTGTAGATTTTTAATATCTCATGATTCTGCCTCCAAGGATGTTTAAAATCTA
         1400                                                    1450
GTTGGGAAAACAAACTTCATCAAGAGTAAATGCAGTGGCATGCTAAGTACCCAAATAGGAGTGTATGCAGAGGATGAAAG
                                                                             1550
ATTAAGATTATGCTCTGGCATCTAACATATGATTCTGTAGTATGAATGTAATCAGTGTATGTTAGTACAAATGTCTATCC
                            1600
ACAGGCTAACCCCCACTCTATGAATCAATAGAAGAAGCTATGACCTTTTGCTGAAATATCAGTTACTGAACAGGCAGGCCA
                                                                1700
CTTTGCCCTCTAAATTACCTCTGATAATTCTAGAGATTTTACCATATTTCTAAACTTTGTTTATAACTCTGAGAAGATCAT
                            1750
ATTTATGTAAAGTATATGTATTTGAGTGCAGAATTTAAATAAGGCTCTACCTCAAAGACCTTTGCACAGTTTATTGGTGT
```

Fig. 2B

```
       1800                                    1850                                    1900
CATATTATACAATATTCAATTGTGAATTCACATAGAAAACATTAAATTATAAGTTTGACTATTATATATGTGTATGCATTTTACTGGCTCAAAACTACCTACTTCTTTCTCAGGCATCAAAAGCATTTTGAGCAGGAGAGTATTACTAGAGCTTTGCC
                                                                              1950
       1950                                    2000                                    2050
ACCTCTCCATTTTTGCCTTGGTGCTCATCTTAATGGCCTAATGCACCCCCAAACATGGAAATATCACCAAAAATACTTAATAGTCCACCAAAAGGCAAGACTGCCCTTAGAAATTCTAGCCTGGTTTGGAGATACTAACTGCTCTCAGAGAAAGTAGCT
                                                                              2100
       2100                                    2150                                    2200
TTGTGACATGTCATGAACCCATGTTTGCAATCAAAGATGATAAAATAGATTCTTATTTTCCCCACCCCCGAAAATGTTCAATAATGTCCCATGTAAAACCTGCTACAAATGGCAGCTTATACATAGCAATGGTAAATCATCATCTGGATTTAGGAAT
                                                                              2250
       2250                                    2300                                    2350
TGCTCTTGTCATACCCTCAAGTTTCTAAGATTTAAGATTCTCCCTACTATCCTACGTTTAAATATCTTTGAAAGTTTGTATTAAAATGTGAATTTTAAGAAATAATATTTATATTTCTGTAAATGTAAACTGTGAAGATAGTTATAAACTGAAGCAGA
                                                                              2400
       2400                                    2450                                    2500
TACCTGGAACCACCTAAAGAACTTCCATTTATGGAGGATTTTTTTGCCCCTTGTGTTTGGAATTATAAAATATAGGTAAA

AGTACGTAATTAAATAAATGTTTTTG
```

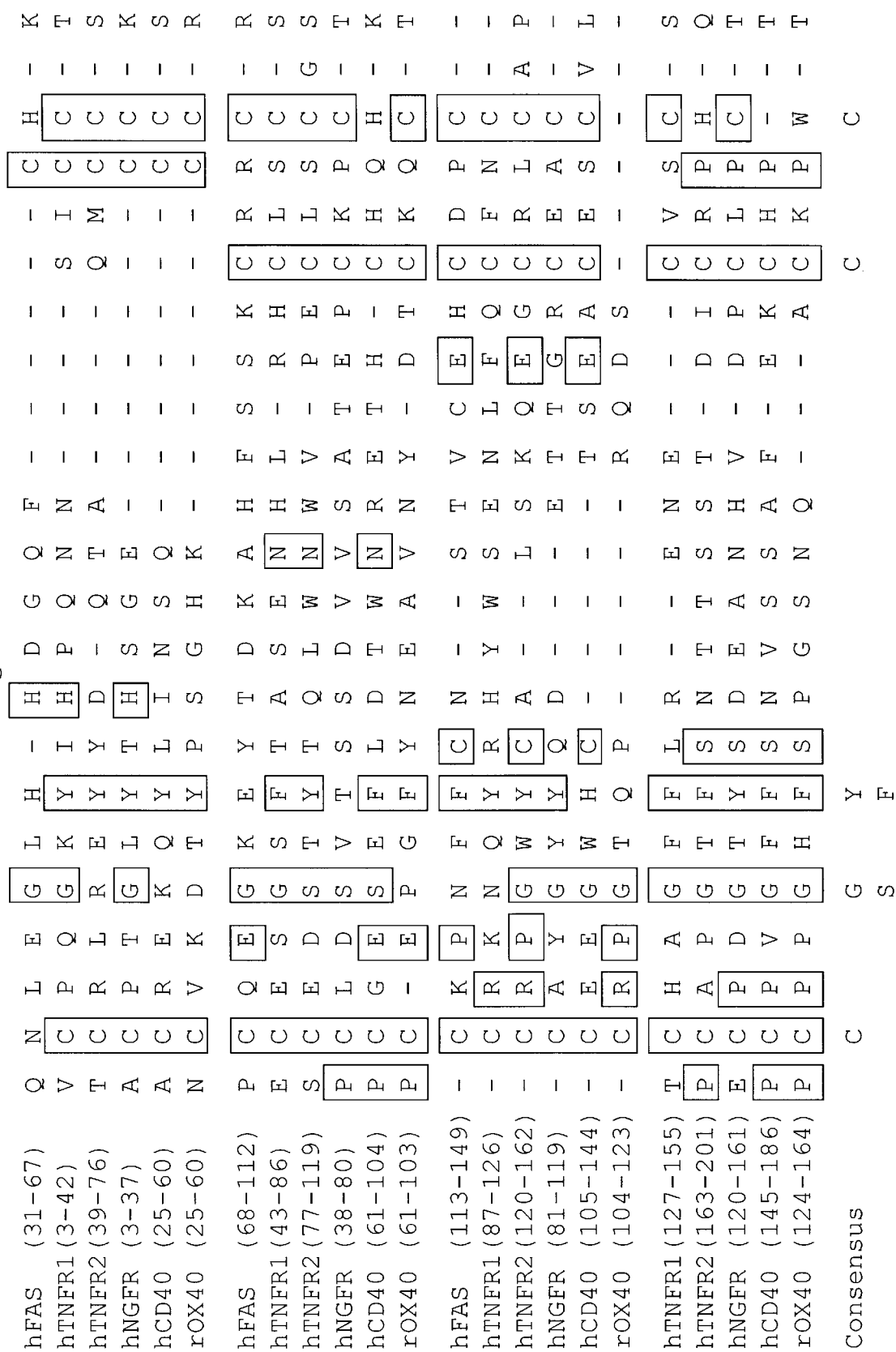

Fig. 8B

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
        ( A ) LENGTH: 2534 base pairs
        ( B ) TYPE: nucleic acid
        ( C ) STRANDEDNESS: double
        ( D ) TOPOLOGY: linear ( i i ) MOLECULE TYPE: cDNA to mRNA ( v i ) ORIGINAL SOURCE:
        ( A ) ORGANISM: Homo sapiens ( v i i ) IMMEDIATE SOURCE:
        ( A ) LIBRARY: pCEV4
        ( B ) CLONE: clone pF58

( i x ) FEATURE:
        ( A ) NAME/KEY: CDS
        ( B ) LOCATION: 195..1202
        ( C ) IDENTIFICATION METHOD: by similarity with known sequence
            or to an established consensus ( i x ) FEATURE:
        ( A ) NAME/KEY: sig_peptide
        ( B ) LOCATION: 195..242
        ( C ) IDENTIFICATION METHOD: by similarity with known sequence
            or to an established consensus ( i x ) FEATURE:
        ( A ) NAME/KEY: mat_peptide
        ( B ) LOCATION: 243..1199
        ( C ) IDENTIFICATION METHOD: by similarity with known sequence
            or to an established consensus ( i x ) FEATURE:
        ( A ) NAME/KEY: polyA_site
        ( B ) LOCATION: 1831..1836
        ( C ) IDENTIFICATION METHOD: by similarity with known sequence
            or to an established consensus ( i x ) FEATURE:
        ( A ) NAME/KEY: polyA_site
        ( B ) LOCATION: 2352..2357
        ( C ) IDENTIFICATION METHOD: by similarity with known sequence
            or to an established consensus ( i x ) FEATURE:
        ( A ) NAME/KEY: polyA_site
        ( B ) LOCATION: 2518..2523
        ( C ) IDENTIFICATION METHOD: by similarity with known sequence
            or to an established consensus ( x i ) SEQUENCE DESCRIPTION: SEQ ID NO:1:

```
GACGCTTCTG  GGGAGTGAGG  GAAGCGGTTT  ACGAGTGACT  TGGCTGGAGC  CTCAGGGGCG       60

GGCACTGGCA  CGGAACACAC  CCTGAGGCCA  GCCCTGGCTG  CCCAGGCGGA  GCTGCCTCTT      120

CTCCCGCGGG  TTGGTGGACC  CGCTCAGTAC  GGAGTTGGGG  AAGCTCTTTC  ACTTCGGAGG      180

ATTGCTCAAC  AACC ATG CTG GGC ATC TGG ACC CTC CTA CCT CTG GTT CTT            230
              Met Leu Gly Ile Trp Thr Leu Leu Pro Leu Val Leu
              -16 -15              -10                     -5

ACG TCT GTT GCT AGA TTA TCG TCC AAA AGT GTT AAT GCC CAA GTG ACT             278
Thr Ser Val Ala Arg Leu Ser Ser Lys Ser Val Asn Ala Gln Val Thr
                 1              5                    10

GAC ATC AAC TCC AAG GGA TTG GAA TTG AGG AAG ACT GTT ACT ACA GTT             326
Asp Ile Asn Ser Lys Gly Leu Glu Leu Arg Lys Thr Val Thr Thr Val
         15                  20                 25
```

| | | | | | | | | | | | | | | | | |
|---|---|---|---|---|---|---|---|---|---|---|---|---|---|---|---|---|
| GAG | ACT | CAG | AAC | TTG | GAA | GGC | CTG | CAT | CAT | GAT | GGC | CAA | TTC | TGC | CAT | 374 |
| Glu | Thr | Gln | Asn | Leu | Glu | Gly | Leu | His | His | Asp | Gly | Gln | Phe | Cys | His | |
| | 30 | | | | 35 | | | | | 40 | | | | | | |
| AAG | CCC | TGT | CCT | CCA | GGT | GAA | AGG | AAA | GCT | AGG | GAC | TGC | ACA | GTC | AAT | 422 |
| Lys | Pro | Cys | Pro | Pro | Gly | Glu | Arg | Lys | Ala | Arg | Asp | Cys | Thr | Val | Asn | |
| 45 | | | | | 50 | | | | | 55 | | | | | 60 | |
| GGG | GAT | GAA | CCA | GAC | TGC | GTG | CCC | TGC | CAA | GAA | GGG | AAG | GAG | TAC | ACA | 470 |
| Gly | Asp | Glu | Pro | Asp | Cys | Val | Pro | Cys | Gln | Glu | Gly | Lys | Glu | Tyr | Thr | |
| | | | | 65 | | | | | 70 | | | | | 75 | | |
| GAC | AAA | GCC | CAT | TTT | TCT | TCC | AAA | TGC | AGA | AGA | TGT | AGA | TTG | TGT | GAT | 518 |
| Asp | Lys | Ala | His | Phe | Ser | Ser | Lys | Cys | Arg | Arg | Cys | Arg | Leu | Cys | Asp | |
| | | | 80 | | | | | 85 | | | | | 90 | | | |
| GAA | GGA | CAT | GGC | TTA | GAA | GTG | GAA | ATA | AAC | TGC | ACC | CGG | ACC | CAG | AAT | 566 |
| Glu | Gly | His | Gly | Leu | Glu | Val | Glu | Ile | Asn | Cys | Thr | Arg | Thr | Gln | Asn | |
| | | 95 | | | | | 100 | | | | | 105 | | | | |
| ACC | AAG | TGC | AGA | TGT | AAA | CCA | AAC | TTT | TTT | TGT | AAC | TCT | ACT | GTA | TGT | 614 |
| Thr | Lys | Cys | Arg | Cys | Lys | Pro | Asn | Phe | Phe | Cys | Asn | Ser | Thr | Val | Cys | |
| | 110 | | | | | 115 | | | | | 120 | | | | | |
| GAA | CAC | TGT | GAC | CCT | TGC | ACC | AAA | TGT | GAA | CAT | GGA | ATC | ATC | AAG | GAA | 662 |
| Glu | His | Cys | Asp | Pro | Cys | Thr | Lys | Cys | Glu | His | Gly | Ile | Ile | Lys | Glu | |
| 125 | | | | | 130 | | | | | 135 | | | | | 140 | |
| TGC | ACA | CTC | ACC | AGC | AAC | ACC | AAG | TGC | AAA | GAG | GAA | GGA | TCC | AGA | TCT | 710 |
| Cys | Thr | Leu | Thr | Ser | Asn | Thr | Lys | Cys | Lys | Glu | Glu | Gly | Ser | Arg | Ser | |
| | | | | 145 | | | | | 150 | | | | | 155 | | |
| AAC | TTG | GGG | TGG | CTT | TGT | CTT | CTT | CTT | TTG | CCA | ATT | CCA | CTA | ATT | GTT | 758 |
| Asn | Leu | Gly | Trp | Leu | Cys | Leu | Leu | Leu | Leu | Pro | Ile | Pro | Leu | Ile | Val | |
| | | | 160 | | | | | 165 | | | | | 170 | | | |
| TGG | GTG | AAG | AGA | AAG | GAA | GTA | CAG | AAA | ACA | TGC | AGA | AAG | CAC | AGA | AAG | 806 |
| Trp | Val | Lys | Arg | Lys | Glu | Val | Gln | Lys | Thr | Cys | Arg | Lys | His | Arg | Lys | |
| | | 175 | | | | | 180 | | | | | 185 | | | | |
| GAA | AAC | CAA | GGT | TCT | CAT | GAA | TCT | CCA | ACC | TTA | AAT | CCT | GAA | ACA | GTG | 854 |
| Glu | Asn | Gln | Gly | Ser | His | Glu | Ser | Pro | Thr | Leu | Asn | Pro | Glu | Thr | Val | |
| | 190 | | | | | 195 | | | | | 200 | | | | | |
| GCA | ATA | AAT | TTA | TCT | GAT | GTT | GAC | TTG | AGT | AAA | TAT | ATC | ACC | ACT | ATT | 902 |
| Ala | Ile | Asn | Leu | Ser | Asp | Val | Asp | Leu | Ser | Lys | Tyr | Ile | Thr | Thr | Ile | |
| 205 | | | | | 210 | | | | | 215 | | | | | 220 | |
| GCT | GGA | GTC | ATG | ACA | CTA | AGT | CAA | GTT | AAA | GGC | TTT | GTT | CGA | AAG | AAT | 950 |
| Ala | Gly | Val | Met | Thr | Leu | Ser | Gln | Val | Lys | Gly | Phe | Val | Arg | Lys | Asn | |
| | | | | 225 | | | | | 230 | | | | | 235 | | |
| GGT | GTC | AAT | GAA | GCC | AAA | ATA | GAT | GAG | ATC | AAG | AAT | GAC | AAT | GTC | CAA | 998 |
| Gly | Val | Asn | Glu | Ala | Lys | Ile | Asp | Glu | Ile | Lys | Asn | Asp | Asn | Val | Gln | |
| | | | 240 | | | | | 245 | | | | | 250 | | | |
| GAC | ACA | GCA | GAA | CAG | AAA | GTT | CAA | CTG | CTT | CGT | AAT | TGG | CAT | CAA | CTT | 1046 |
| Asp | Thr | Ala | Glu | Gln | Lys | Val | Gln | Leu | Leu | Arg | Asn | Trp | His | Gln | Leu | |
| | | 255 | | | | | 260 | | | | | 265 | | | | |
| CAT | GGA | AAG | AAA | GAA | GCG | TAT | GAC | ACA | TTG | ATT | AAA | GAT | CTC | AAA | AAA | 1094 |
| His | Gly | Lys | Lys | Glu | Ala | Tyr | Asp | Thr | Leu | Ile | Lys | Asp | Leu | Lys | Lys | |
| | 270 | | | | | 275 | | | | | 280 | | | | | |
| GCC | AAT | CTT | TGT | ACT | CTT | GCA | GAG | AAA | ATT | CAG | ACT | ATC | ATC | CTC | AAG | 1142 |
| Ala | Asn | Leu | Cys | Thr | Leu | Ala | Glu | Lys | Ile | Gln | Thr | Ile | Ile | Leu | Lys | |
| 285 | | | | | 290 | | | | | 295 | | | | | 300 | |
| GAC | ATT | ACT | AGT | GAC | TCA | GAA | AAT | TCA | AAC | TTC | AGA | AAT | GAA | ATC | CAA | 1190 |
| Asp | Ile | Thr | Ser | Asp | Ser | Glu | Asn | Ser | Asn | Phe | Arg | Asn | Glu | Ile | Gln | |
| | | | | 305 | | | | | 310 | | | | | 315 | | |
| AGC | TTG | GTC | TAGAGTGAAA | AACAACAAAT | TCAGTTCTGA | GTATATGCAA | | | | | | | | | | 1239 |
| Ser | Leu | Val | | | | | | | | | | | | | | |
| TTAGTGTTTG | AAAAGATTCT | TAATAGCTGG | CTGTAAATAC | TGCTTGGTTT | TTTACTGGGT | | | | | | | | | | | 1299 |
| ACATTTTATC | ATTTATTAGC | GCTGAAGAGC | CAACATATTT | GTAGATTTTT | AATATCTCAT | | | | | | | | | | | 1359 |

|  |  |  |  |  |  |  |
|---|---|---|---|---|---|---|
| GATTCTGCCT | CCAAGGATGT | TTAAAATCTA | GTTGGGAAAA | CAAACTTCAT | CAAGAGTAAA | 1419 |
| TGCAGTGGCA | TGCTAAGTAC | CCAAATAGGA | GTGTATGCAG | AGGATGAAAG | ATTAAGATTA | 1479 |
| TGCTCTGGCA | TCTAACATAT | GATTCTGTAG | TATGAATGTA | ATCAGTGTAT | GTTAGTACAA | 1539 |
| ATGTCTATCC | ACAGGCTAAC | CCCACTCTAT | GAATCAATAG | AAGAAGCTAT | GACCTTTTGC | 1599 |
| TGAAATATCA | GTTACTGAAC | AGGCAGGCCA | CTTTGCCTCT | AAATTACCTC | TGATAATTCT | 1659 |
| AGAGATTTTA | CCATATTTCT | AAACTTTGTT | TATAACTCTG | AGAAGATCAT | ATTTATGTAA | 1719 |
| AGTATATGTA | TTTGAGTGCA | GAATTTAAAT | AAGGCTCTAC | CTCAAAGACC | TTTGCACAGT | 1779 |
| TTATTGGTGT | CATATTATAC | AATATTTCAA | TTGTGAATTC | ACATAGAAAA | CATTAAATTA | 1839 |
| TAATGTTTGA | CTATTATATA | TGTGTATGCA | TTTTACTGGC | TCAAAACTAC | CTACTTCTTT | 1899 |
| CTCAGGCATC | AAAAGCATTT | TGAGCAGGAG | AGTATTACTA | GAGCTTTGCC | ACCTCTCCAT | 1959 |
| TTTTGCCTTG | GTGCTCATCT | TAATGGCCTA | ATGCACCCCC | AAACATGGAA | ATATCACCAA | 2019 |
| AAAATACTTA | ATAGTCCACC | AAAAGGCAAG | ACTGCCCTTA | GAAATTCTAG | CCTGGTTTGG | 2079 |
| AGATACTAAC | TGCTCTCAGA | GAAAGTAGCT | TTGTGACATG | TCATGAACCC | ATGTTTGCAA | 2139 |
| TCAAAGATGA | TAAAATAGAT | TCTTATTTTT | CCCCCACCCC | CGAAAATGTT | CAATAATGTC | 2199 |
| CCATGTAAAA | CCTGCTACAA | ATGGCAGCTT | ATACATAGCA | ATGGTAAAAT | CATCATCTGG | 2259 |
| ATTTAGGAAT | TGCTCTTGTC | ATACCCTCAA | GTTCTAAGA | TTTAAGATTC | TCCTTACTAC | 2319 |
| TATCCTACGT | TTAAATATCT | TTGAAAGTTT | GTATTAAATG | TGAATTTTAA | GAAATAATAT | 2379 |
| TTATATTTCT | GTAAATGTAA | ACTGTGAAGA | TAGTTATAAA | CTGAAGCAGA | TACCTGGAAC | 2439 |
| CACCTAAAGA | ACTTCCATTT | ATGGAGGATT | TTTTTGCCCC | TTGTGTTTGG | AATTATAAAA | 2499 |
| TATAGGTAAA | AGTACGTAAT | TAAATAATGT | TTTTG |  |  | 2534 |

( 2 ) INFORMATION FOR SEQ ID NO:2:

( i ) SEQUENCE CHARACTERISTICS:
        ( A ) LENGTH: 335 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met  Leu  Gly  Ile  Trp  Thr  Leu  Leu  Pro  Leu  Val  Leu  Thr  Ser  Val  Ala
-16  -15                      -10                      -5

Arg  Leu  Ser  Ser  Lys  Ser  Val  Asn  Ala  Gln  Val  Thr  Asp  Ile  Asn  Ser
  1             5                      10                      15

Lys  Gly  Leu  Glu  Leu  Arg  Lys  Thr  Val  Thr  Val  Glu  Thr  Gln  Asn
               20                 25                      30

Leu  Glu  Gly  Leu  His  His  Asp  Gly  Gln  Phe  Cys  His  Lys  Pro  Cys  Pro
               35                 40                      45

Pro  Gly  Glu  Arg  Lys  Ala  Arg  Asp  Cys  Thr  Val  Asn  Gly  Asp  Glu  Pro
          50                 55                      60

Asp  Cys  Val  Pro  Cys  Gln  Glu  Gly  Lys  Glu  Tyr  Thr  Asp  Lys  Ala  His
 65                      70                      75                      80

Phe  Ser  Ser  Lys  Cys  Arg  Arg  Cys  Arg  Leu  Cys  Asp  Glu  Gly  His  Gly
                    85                      90                      95

Leu  Glu  Val  Glu  Ile  Asn  Cys  Thr  Arg  Thr  Gln  Asn  Thr  Lys  Cys  Arg
              100                     105                     110

Cys  Lys  Pro  Asn  Phe  Phe  Cys  Asn  Ser  Thr  Val  Cys  Glu  His  Cys  Asp
          115                     120                     125

Pro  Cys  Thr  Lys  Cys  Glu  His  Gly  Ile  Ile  Lys  Glu  Cys  Thr  Leu  Thr
```

```
                130                      135                     140
Ser  Asn  Thr  Lys  Cys  Lys  Glu  Glu  Gly  Ser  Arg  Ser  Asn  Leu  Gly  Trp
145                      150                      155                     160

Leu  Cys  Leu  Leu  Leu  Leu  Pro  Ile  Pro  Leu  Ile  Val  Trp  Val  Lys  Arg
                    165                      170                     175

Lys  Glu  Val  Gln  Lys  Thr  Cys  Arg  Lys  His  Arg  Lys  Glu  Asn  Gln  Gly
                180                      185                     190

Ser  His  Glu  Ser  Pro  Thr  Leu  Asn  Pro  Glu  Thr  Val  Ala  Ile  Asn  Leu
          195                      200                     205

Ser  Asp  Val  Asp  Leu  Ser  Lys  Tyr  Ile  Thr  Thr  Ile  Ala  Gly  Val  Met
     210                      215                     220

Thr  Leu  Ser  Gln  Val  Lys  Gly  Phe  Val  Arg  Lys  Asn  Gly  Val  Asn  Glu
225                      230                      235                     240

Ala  Lys  Ile  Asp  Glu  Ile  Lys  Asn  Asp  Asn  Val  Gln  Asp  Thr  Ala  Glu
                    245                      250                     255

Gln  Lys  Val  Gln  Leu  Leu  Arg  Asn  Trp  His  Gln  Leu  His  Gly  Lys  Lys
                260                      265                     270

Glu  Ala  Tyr  Asp  Thr  Leu  Ile  Lys  Asp  Leu  Lys  Lys  Ala  Asn  Leu  Cys
          275                      280                     285

Thr  Leu  Ala  Glu  Lys  Ile  Gln  Thr  Ile  Ile  Leu  Lys  Asp  Ile  Thr  Ser
290                      295                      300

Asp  Ser  Glu  Asn  Ser  Asn  Phe  Arg  Asn  Glu  Ile  Gln  Ser  Leu  Val
305                      310                      315
```

( 2 ) INFORMATION FOR SEQ ID NO:3:

( i ) SEQUENCE CHARACTERISTICS:
        ( A ) LENGTH: 119 amino acids
        ( B ) TYPE: amino acid
        ( D ) TOPOLOGY: linear ( i i ) MOLECULE TYPE: protein ( x i ) SEQUENCE DESCRIPTION: SEQ ID NO:3:

```
Gln  Asn  Leu  Glu  Gly  Leu  His  His  Asp  Gly  Gln  Phe  Cys  His  Lys  Pro
1                   5                        10                      15

Cys  Pro  Pro  Gly  Glu  Arg  Lys  Ala  Arg  Asp  Cys  Thr  Val  Asn  Gly  Asp
                20                       25                      30

Glu  Pro  Asp  Cys  Val  Pro  Cys  Gln  Glu  Gly  Lys  Glu  Tyr  Thr  Asp  Lys
               35                       40                      45

Ala  His  Phe  Ser  Ser  Lys  Cys  Arg  Arg  Cys  Arg  Leu  Cys  Asp  Glu  Gly
          50                      55                       60

His  Gly  Leu  Glu  Val  Glu  Ile  Asn  Cys  Thr  Arg  Thr  Gln  Asn  Thr  Lys
65                       70                      75                      80

Cys  Arg  Cys  Lys  Pro  Asn  Phe  Phe  Cys  Asn  Ser  Thr  Val  Cys  Glu  His
                    85                      90                      95

Cys  Asp  Pro  Cys  Thr  Lys  Cys  Glu  His  Gly  Ile  Ile  Lys  Glu  Cys  Thr
               100                      105                     110

Leu  Thr  Ser  Asn  Thr  Lys  Cys
               115
```

( 2 ) INFORMATION FOR SEQ ID NO:4:

( i ) SEQUENCE CHARACTERISTICS:
        ( A ) LENGTH: 153 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Val Cys Pro Gln Gly Lys Tyr Ile His Pro Gln Asn Asn Ser Ile Cys
1               5                   10                  15

Cys Thr Lys Cys His Lys Gly Thr Tyr Leu Tyr Asn Asp Cys Pro Gly
            20                  25                  30

Pro Gly Gln Asp Thr Asp Cys Arg Glu Cys Glu Ser Gly Ser Phe Thr
        35                  40                  45

Ala Ser Glu Asn His Leu Arg His Cys Leu Ser Cys Ser Lys Cys Arg
    50                  55                  60

Lys Glu Met Gly Gln Val Glu Ile Ser Ser Cys Thr Val Asp Arg Asp
65                  70                  75                  80

Thr Val Cys Gly Cys Arg Lys Asn Gln Tyr Arg His Tyr Trp Ser Glu
                85                  90                  95

Asn Leu Phe Gln Cys Phe Asn Cys Ser Leu Cys Leu Asn Gly Thr Val
            100                 105                 110

His Leu Ser Cys Gln Glu Lys Gln Asn Thr Val Cys Thr Cys His Ala
        115                 120                 125

Gly Phe Phe Leu Arg Glu Asn Glu Cys Val Ser Cys Ser Asn Cys Lys
    130                 135                 140

Lys Ser Leu Glu Cys Thr Lys Leu Cys
145                 150
```

( 2 ) INFORMATION FOR SEQ ID NO:5:

( i ) SEQUENCE CHARACTERISTICS:
( A ) LENGTH: 163 amino acids
( B ) TYPE: amino acid
( D ) TOPOLOGY: linear ( i i ) MOLECULE TYPE: protein ( x i ) SEQUENCE DESCRIPTION: SEQ ID NO:5:

```
Thr Cys Arg Leu Arg Glu Tyr Tyr Asp Gln Thr Ala Gln Met Cys Cys
1               5                   10                  15

Ser Lys Cys Ser Pro Gly Gln His Ala Lys Val Phe Cys Thr Lys Thr
            20                  25                  30

Ser Asp Thr Val Cys Asp Ser Cys Glu Asp Ser Thr Tyr Thr Gln Leu
        35                  40                  45

Trp Asn Trp Val Pro Glu Cys Leu Ser Cys Gly Ser Arg Cys Ser Asp
    50                  55                  60

Asp Gln Val Glu Thr Gln Ala Cys Thr Arg Glu Gln Asn Arg Ile Cys
65                  70                  75                  80

Thr Cys Arg Pro Gly Trp Tyr Cys Ala Leu Ser Lys Gln Glu Gly Cys
                85                  90                  95

Arg Leu Cys Ala Pro Leu Arg Lys Cys Arg Pro Gly Phe Gly Val Ala
            100                 105                 110

Arg Pro Gly Thr Glu Thr Ser Asp Val Val Cys Lys Pro Cys Ala Pro
        115                 120                 125

Gly Thr Phe Ser Asn Thr Thr Ser Ser Thr Asp Ile Cys Arg Pro His
    130                 135                 140

Gln Ile Cys Asn Val Val Ala Ile Pro Gly Asn Ala Ser Met Asp Ala
145                 150                 155                 160

Val Cys Thr
```

( 2 ) INFORMATION FOR SEQ ID NO:6:

( i ) SEQUENCE CHARACTERISTICS:
    ( A ) LENGTH: 159 amino acids
    ( B ) TYPE: amino acid
    ( D ) TOPOLOGY: linear ( i i ) MOLECULE TYPE: protein ( x i ) SEQUENCE DESCRIPTION: SEQ ID NO:6:

```
Ala Cys Pro Thr Gly Leu Tyr Thr His Ser Gly Glu Cys Cys Lys Ala
 1               5                  10                  15
Cys Asn Leu Gly Glu Gly Val Ala Gln Pro Cys Gly Ala Asn Gln Thr
                20                  25                  30
Val Cys Glu Pro Cys Leu Asp Ser Val Thr Ser Ser Asp Val Val Ser
            35                  40                  45
Ala Thr Glu Pro Cys Lys Pro Cys Thr Glu Cys Val Gly Leu Gln Ser
        50                  55                  60
Met Ser Ala Pro Cys Val Glu Ala Asp Ala Val Cys Arg Cys Ala
 65                 70                  75                  80
Tyr Gly Tyr Tyr Gln Asp Glu Thr Thr Gly Arg Cys Glu Ala Cys Arg
                85                  90                  95
Val Cys Glu Ala Gly Ser Gly Leu Val Phe Ser Cys Gln Asp Lys Gln
            100                 105                 110
Asn Thr Val Cys Glu Glu Cys Pro Asp Gly Thr Tyr Ser Asp Glu Ala
        115                 120                 125
Asn His Val Asp Pro Cys Leu Pro Cys Thr Val Cys Glu Asp Thr Glu
    130                 135                 140
Arg Gln Leu Arg Glu Cys Thr Arg Trp Ala Asp Ala Glu Cys Glu
145                 150                 155
```

( 2 ) INFORMATION FOR SEQ ID NO:7:

( i ) SEQUENCE CHARACTERISTICS:
    ( A ) LENGTH: 162 amino acids
    ( B ) TYPE: amino acid
    ( D ) TOPOLOGY: linear ( i i ) MOLECULE TYPE: protein ( x i ) SEQUENCE DESCRIPTION: SEQ ID NO:7:

```
Ala Cys Arg Glu Lys Gln Tyr Leu Ile Asn Ser Gln Cys Cys Ser Leu
 1               5                  10                  15
Cys Gln Pro Gly Gln Lys Leu Val Ser Asp Cys Thr Glu Phe Thr Glu
                20                  25                  30
Thr Glu Cys Leu Pro Cys Gly Glu Ser Glu Phe Leu Asp Thr Trp Asn
            35                  40                  45
Arg Glu Thr His Cys His Gln His Lys Tyr Cys Asp Pro Asn Leu Gly
        50                  55                  60
Leu Arg Val Gln Gln Lys Gly Thr Ser Glu Thr Asp Thr Ile Cys Thr
 65                 70                  75                  80
Cys Glu Glu Gly Trp His Cys Thr Ser Glu Ala Cys Glu Ser Cys Val
                85                  90                  95
Leu His Arg Ser Cys Ser Pro Gly Phe Gly Val Lys Gln Ile Ala Thr
            100                 105                 110
Gly Val Ser Asp Thr Ile Cys Glu Pro Cys Pro Val Gly Phe Phe Ser
        115                 120                 125
Asn Val Ser Ser Ala Phe Glu Lys Cys His Pro Thr Ser Cys Glu Thr
    130                 135                 140
Lys Asp Leu Val Val Gln Gln Ala Gly Thr Asn Lys Thr Asp Val Val
145                 150                 155                 160
```

Cys  Gly ( 2 ) INFORMATION FOR SEQ ID NO:8:

( i ) SEQUENCE CHARACTERISTICS:
        ( A ) LENGTH: 139 amino acids
        ( B ) TYPE: amino acid
        ( D ) TOPOLOGY: linear ( i i ) MOLECULE TYPE: protein ( x i ) SEQUENCE DESCRIPTION: SEQ ID NO:8:

Asn  Cys  Val  Lys  Asp  Thr  Tyr  Pro  Ser  Gly  His  Lys  Cys  Arg  Glu  Cys
    1                   5                        10                       15

Gln  Pro  Gly  His  Gly  Met  Val  Ser  Arg  Cys  Asp  His  Thr  Arg  Asp  Thr
                   20                       25                       30

Val  Cys  His  Pro  Cys  Glu  Pro  Gly  Phe  Tyr  Asn  Glu  Ala  Val  Asn  Tyr
              35                       40                       45

Asp  Thr  Cys  Lys  Gln  Cys  Thr  Gln  Cys  Asn  His  Arg  Ser  Gly  Ser  Glu
         50                       55                       60

Leu  Lys  Gln  Asn  Cys  Thr  Pro  Thr  Glu  Asp  Thr  Val  Cys  Gln  Cys  Arg
    65                       70                       75                       80

Pro  Gly  Thr  Gln  Pro  Arg  Gln  Asp  Ser  Ser  His  Lys  Leu  Gly  Val  Asp
                   85                       90                       95

Cys  Val  Pro  Cys  Pro  Pro  Gly  His  Phe  Ser  Pro  Gly  Ser  Asn  Gln  Ala
                   100                      105                      110

Cys  Lys  Pro  Trp  Thr  Asn  Cys  Thr  Leu  Ser  Gly  Lys  Gln  Ile  Arg  His
                   115                      120                      125

Pro  Ala  Ser  Asn  Ser  Leu  Asp  Thr  Val  Cys  Glu
         130                      135

( 2 ) INFORMATION FOR SEQ ID NO:9:

( i ) SEQUENCE CHARACTERISTICS:
        ( A ) LENGTH: 45 amino acids
        ( B ) TYPE: amino acid
        ( D ) TOPOLOGY: linear ( i i ) MOLECULE TYPE: protein ( x i ) SEQUENCE DESCRIPTION: SEQ ID NO:9:

Lys  Ala  Pro  His  Pro  Lys  Gln  Glu  Pro  Gln  Glu  Ile  Asn  Phe  Pro  Asp
    1                   5                        10                       15

Asp  Leu  Pro  Gly  Ser  Asn  Thr  Ala  Ala  Pro  Val  Gln  Glu  Thr  Leu  His
                   20                       25                       30

Gly  Cys  Gln  Pro  Val  Thr  Gln  Glu  Asp  Gly  Lys  Glu  Ser
              35                       40                       45

( 2 ) INFORMATION FOR SEQ ID NO:10:

( i ) SEQUENCE CHARACTERISTICS:
        ( A ) LENGTH: 45 amino acids
        ( B ) TYPE: amino acid
        ( D ) TOPOLOGY: linear ( i i ) MOLECULE TYPE: protein ( x i ) SEQUENCE DESCRIPTION: SEQ ID NO:10:

Lys  Gly  Phe  Val  Arg  Lys  Asn  Gly  Val  Asn  Glu  Ala  Lys  Ile  Asp  Glu
    1                   5                        10                       15

Ile  Lys  Asn  Asp  Asn  Val  Gln  Asp  Thr  Ala  Glu  Gln  Lys  Val  Gln  Leu
                   20                       25                       30

-continued

```
Leu  Arg  Asn  Trp  His  Gln  Leu  His  Gly  Lys  Lys  Glu  Ala
          35                      40                      45
```

( 2 ) INFORMATION FOR SEQ ID NO:11:

( i ) SEQUENCE CHARACTERISTICS:
        ( A ) LENGTH: 45 amino acids
        ( B ) TYPE: amino acid
        ( D ) TOPOLOGY: linear ( i i ) MOLECULE TYPE: protein ( x i ) SEQUENCE DESCRIPTION: SEQ ID NO:11:

```
Lys  Glu  Phe  Val  Arg  Arg  Leu  Gly  Leu  Ser  Asp  His  Glu  Ile  Asp  Arg
1              5                        10                       15

Leu  Glu  Leu  Gln  Asn  Gly  Arg  Cys  Leu  Arg  Glu  Ala  Gln  Tyr  Ser  Met
               20                       25                       30

Leu  Ala  Thr  Trp  Arg  Arg  Arg  Thr  Pro  Arg  Arg  Glu  Ala
          35                      40                      45
```

FAS ANTIGEN

This application is a continuation of application Ser. No. 07/872,129, filed Apr. 22, 1992 now abandoned.

FIELD OF THE INVENTION

The present invention relates to DNAs coding for human cell surface antigen (hereinafter referred to as Fas or Fas antigen) and to vectors for expressing for said DNAs.

BACKGROUND OF THE INVENTION

Fas is a polypeptide that exists in the surfaces of a variety of cells and is considered to be deeply concerned with the apoptosis of cells. The apoptosis is a form of death of cells that is distinguished from the so-called necrosis of cells, and is observed at the time of death of various cells such as of embryogenesis, metamorphosis, endocrine-dependent tissue atrophy and turnover of normal tissues [Wyllie et al. Int. Rev. Cytol. 68, 251–306, 1980; Walker et al. Meth. Achiev. Exp. Pathol. 13, 18–54, 1988; Schmidt et al. Proc. Natl. Acad. Sci. USA 83, 1881–1885, 1986; Ucker et al. Nature 327, 62–64, 1987; Smith et al. Nature 337, 181–184, 1989; Williams et al. Nature 343, 76–79, 1990]. The following features have been pointed out as a result of the morphological and biochemical analyses of cells at the apoptosis:

The apoptosis is accompanied by condensation of cytoplasm, loss of plasma membrane microvilli, segmentation of the nucleus, extensive degradation of chromosomal DNA (into oligomers of about 180 base pair units), and formation of apoptotic bleb [Wyllie et al. 1980 (mentioned above)]. The apoptosis is a physiologically and medically interesting phenomenon because it is a form associated with the death of immunocytes such as thymocytes and the extinction of the tumor cells.

In regression of tumor (alleviation of tumor), in general, the apoptosis mediates the death of target cells by interaction with natural killer cells or cytotoxic T lymphocytes [Duke et al. Proc. Natil. Acad. Sci. USA 80, 6361–6365, 1983; Schmidt et al, 1986 ibid.; Ucker, 1987 (mentioned above)], or by tumor necrosis factor-α (TNF-α) or its related cytokine lymphotoxin (TNF-β) against the target cells [Schmidt et al, 1986 (mentioned above); Dealtry et al. Eur. J. Immunol. 17, 689–693, 1987; Larrick and Wright, FASEB J. 4, 3215–3223, 1990].

With regard to the relationship between the Fas antigen and the apoptosis, the present inventors have previously disclosed that the mouse monoclonal antibody against the human Fas antigen has a cytolytic activity on human cells expressing the Fas antigen while it does not act upon mouse cells [Yonehara et al. J. Exp. Med. 169, 1747–1756, 1989]. It has also been disclosed by Trauth et al. that the anti-Apo-I antibody has effects analogous to those of the anti-Fas antibody [Science 245, 301–305, 1989].

In a recent study by the present inventors, furthermore, it has been found that cells infected with human immunodeficiecy virus (HIV) are more sensitive to the cytocidal activity of the anti-Fas monoclonal antibody than uninfected cells [Kobayashi et al. Proc. Natl. Acad. Sci. USA 87, 9620–9624, 1990]. However, it is still not clear whether the expression of the Fas antigen that is predominant in the infected cells is actually induced by infection with HIV or by a general transformation. It is also considered potential to specifically drive the HIV-infected cells into apoptosis by using a monoclonal antibody specific to Fas antigen.

The present inventors have further discovered that the treatment of human colon carcinoma HT-29 cells with interferon-γ (INF-γ) induces the Fas antigen on the cell surface, and renders the tumor cells more susceptible to the cytotoxic activity of the anti-Fas antibody (Yonehara et al, 1989 (mentioned above)).

As described above, it has been pointed out that the Fas antigen is closely related to the apoptosis but numerous points remain not clarified. Therefore, it is physiologically and pathologically meaningful to disclose the entire structure of the Fas antigen and to clarify its function. It is further considered that various monoclonal antibodies that specifically reacts with Fas may be easily obtained if the structure of the Fas antigen is disclosed, and used in treating diseases associated with HIV infection and malignant tumors to be cured.

Therefore, it is physiologically and pathologically very advantageous to clarify the main body of Fas antigen, to clarify its complete structure and to clarify its function. Furthermore, if the Fas antigen is obtained in large amounts in pure form, it will become possible to more clearly analyze its structure and functions. By utilizing the knowledge related to the thus clarified structure of Fas antigen, it will still become possible to study the Fas antigen analogs by modifying them as well as to utilize in large amounts only those portions essential to the expression of the functions.

With the structure of the Fas antigen being clarified, furthermore, it will become possible to obtain various monoclonal antibodies that specifically reacts with Fas as well as to obtain various ligands, agonists and antagonists related to Fas, and to develop studies with regard to their effects upon the cells and relationships of the structure and activities thereof.

In order to accomplish the above object, it is essential to establish means capable of supplying Fas polypeptides in sufficient amounts. In recent years, a recombinant DNA technology has been utilized as a method for preparing physiologically active substance. In order to prepare the Fas antigen by utilizing the above technology, however, it is necessary to isolate DNA that encodes Fas proteins followed by cloning.

SUMMARY OF THE INVENTION

The present inventors have succeeded in the development of means capable of producing in large amounts the human Fas antigen in pure form. The present inventors have clarified the genes of the human Fas antigen and have disclosed, for the first time, how to genetically manipulate the Fas antigen genes.

The present invention provides DNA coding for human Fas antigens, DNA derived therefrom, and DNA fragments thereof. They may include those having an anti-sense sequence thereof. The present invention further provides products such as proteins and peptides produced by using the DNA that encodes the Fas antigen or by using derivatives thereof.

The invention also provides plasmids or vectors that carry DNA coding for the Fas antigen or DNA derived therefrom or fragments thereof. Moreover, the invention provides a variety of transformants that hold replicably or expressibly the plasmid or the vector therein. The present invention encompasses a variety of products produced by utilizing base sequence information of DNA encoding the Fas antigen.

BRIEF DESCRIPTION OF THE DRAWINGS

FIGS. 1A and B show the nucleotide sequence and predicted amino acid sequence of the cDNA coding human Fas protein (up to 284th amino acid, which are identified in the Sequence Listing as SEQ ID NO: 1 and SEQ ID NO: 2.

FIGS. 2A and B show the nucleotide sequence and predicted amino acid sequence of the cDNA coding human Fas protein (after 284th amino acid, which are identified in the Sequence Listing as SEQ ID NO: 1 and SEQ ID NO: 2).

FIGS. 4A–4F represent WR19L, 58-12a, 58-80d, L929, LB1, and LB11, respectively.

FIG. 8 shows the schematic representation of comparison in amino acid sequence of extracellular domain of the human Fas with other members of the NGFR/TNFR family (see SEQ ID NOS: 3–8).

DETAILED DESCRIPTION OF THE INVENTION

Figure 3A:
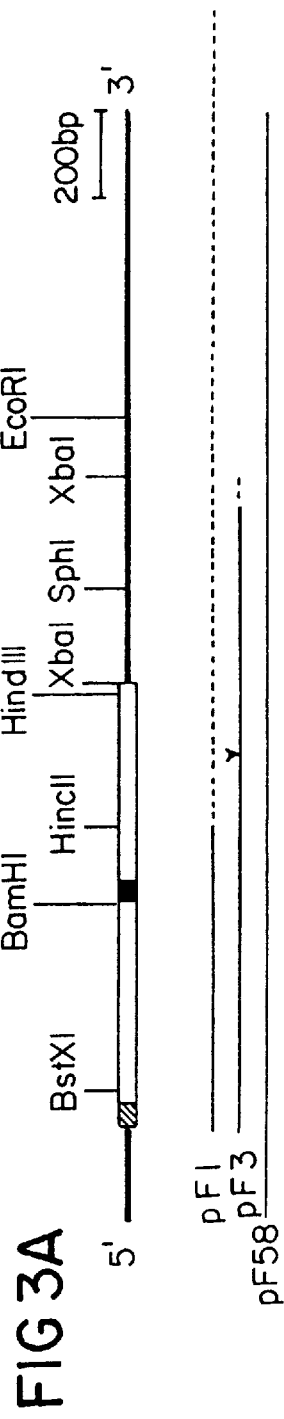
FIG. 3A shows the schematic representation and restriction map of the human Fas cDNA (pF58).

The invention relates to DNA coding for human cell surface antigen or those having substantially the same functions as said human cell surface antigen, DNA derived therefrom or DNA fragmented therefrom. Particularly, the invention relates to DNA coding for Fas antigens, preferably peptides having at least a part of the amino acid sequences, and more preferably the amino acid sequences described in FIGS. 1 and 2 which are identified in the Sequence Listing as SEQ ID NO:1 and SEQ ID NO:2.

Furthermore, the invention relates to DNA comprising at least a part of the base sequences described in FIGS. 1 and 2 which are identified in the Sequence Listing as SEQ ID NO:1 and SEQ ID NO:2, preferably DNA having the base numbers 215 to 1199, 243 to 1199, 215 to 713 or 243 to 713 of FIGS. 1 and 2, or a portion thereof.

The invention still relates to proteins or peptides comprising at least a part of the amino acid sequences having a substantially human cell surface antigen activity, particularly a Fas antigen activity, preferably at least a part of the amino acid sequences described in FIGS. 1 and 2, and more preferably the amino acid numbers −16 to 319, 1 to 319, −16 to 157, or 1 to 157 described in FIGS. 1 and 2 which are identified in the Sequence Listing as SEQ ID NO:1 and SEQ ID NO:2.

The invention also relates to expression vectors comprising the above DNA, transformants transformed by said expression vector and methods for producing said protein or peptide which comprises cultivating said transformant under a suitable condition in a suitable medium and collecting the produced protein or peptide from the cultured medium.

The present invention is also concerned with various reagents for analysis or medical drugs comprising an effective amount of the product such as proteins obtained as described above as well as antigens obtained as described above.

According to the present invention, it would become possible to develop Fas genes or Fas gene analogs in various cells inclusive of human cells by utilizing information related to base sequences of the cDNA clone (for example, pF85) or fragments derived therefrom or base sequences thereof.

It should be comprehended that the present invention is concerned with those that are thus finally obtained. The development can be effected according to methods described in this specification or according to suitably modified methods.

The present inventors have screened a variety of human cell lines in connection with the expression of the Fas antigen and have discovered that human T cell lymphoma KT-3 expresses the Fas antigen about 20 times as much as other cell strains. The inventors have succeeded in isolating and cloning cDNAs encoding human Fas antigen determinant from human T cell lymphoma KT-3 cells.

FIGS. 1 and 2 show a cDNA nucleotide sequence and predicted amino acid sequence from a human Fas antigen cDNA clone (pF 58) that is obtained herein.

FIG. 3 shows a restriction map of cDNA (pF 58) for human Fas antigen.

The transformant (*Esherichia coli*, pF 58) carrying the plasmid pF 58 was originally deposited as a domestic microorganism deposit (FERM P-12192) at the Fermentation Research Institute, Agency of Industrial Science and Technology, Ministry of International Trade and Industry, Japan (FRI) on Apr. 12, 1991 and converted into an international one (FERM BP-3826) under the Budapest Treaty.

The above pF58 cDNA has an open reading frame that is capable of encoding a protein consisting of 335 amino acids. From the predicted amino acid sequence, it is estimated that the mature Fas antigen is a protein consisting of 319 amino acids and is constituted by an extracellular domain, a transmembrane domain and a cytoplasmic domain. Such a constitution is common to many cell surface receptors. As will be described later, it was confirmed through the comparison of the amino acid sequence of the Fas protein with amino acid sequences of other cell surface proteins that the above Fas protein pertains to an NGFR/TNFR family in the group of cell surface membrane proteins.

A lot of cell surface receptors have heretofore been discovered, and targetting molecules including monoclonal antibodies against the receptor or various ligands related thereto or derivatives of the receptor or analogs thereof have been developed in the art. Furthermore, extensive investigations have been made on the development of methods for the treatment or diagnosis of deseases by using such products.

For instance, it has been known that CD4 which is a cell surface antigen of lymphocytes works as a receptor when the cells are infected with human immunodeficiency virus (HIV), AIDS virus. It has been reported by many researchers that the soluble mutant CD4 having a binding region to HIV, which is derived from natural CD4 by a genetic engineering based upon the above knowledge, may weaken the HIV infectivity or cytopathic effect [Smith, DH. et al., Science 238: 1704–1707, 1987; Fisher, RA. et al., Nature 331: 76–78, 1988; Hussey RE. et al. Nature 331: 78–81, 1988; Deen, KC. et al. Nature 331: 82–84, 1988; Traunecker, A. et al., Nature 331: 84–86, 1988; Manca F. et al, Lancet 335: 811–815, 1990].

Furthermore, Olsson, I. et al. reports general thesis concerning the receptors of hematopoetic control factors [Eur. J. Haematol. 48: 1–9, 1992] in which they disclose that a variety of receptors exist in a soluble form in the living body. The TNF-binding protein found in urea is a soluble TNF receptor which exists on the cell surface and which is liberated from the cells by the action of a proteolytic enzyme. In the case of an M-CSF receptor, protein kinase C is activated, thereby the transmembrane domain of the receptor being cut and the soluble receptor consisting of an extracellular domain alone being emitted. There is a mRNA coding for the soluble proteins of IL-4 and IL-7 receptors in cells. It is confirmed that there is even a mRNA without the sequence coding for a transmembrane domain of the M-CSF in U-937 cells. Concerning the physiological meaning of the presence of such molecules in the living body, they have estimated that the soluble TNF receptor regulates the physiological activity of TNF that is emitted in vivo and suggested clinical applications such as application to endotoxin shock therapy in which it is becoming apparent that TNF strongly participates in the development of the disease.

A variety of discoveries have also been reported concerning the IL-2 receptor. For instance, according to Soulillou, JP. et al. [Transpl. Int. 2(1): 46–52, 1989], the monoclonal antibody that inhibits the bonding of IL-2 to IL-2 receptor is effective in controlling the rejection when the organs are transplanted. It is considered that such a monoclonal antibody is an antagonist against the IL-2 receptor in a broad sense. Rubin, LA. et al. reports that measurement of the concentration of soluble IL-2 receptors in the blood is effective in diagnosing or comprehending the condition of blood cancers, AIDS, rheumatic diseases, or various inflammations and infections [Anal. Intern. Med. 113: 619–627, 1990].

Concerning the IL-1 receptor, it has been reported that what is called natural IL-1 receptor antagonist exists in the living body [Arend, WP. et al., Br. J. Rheumatol. 30 suppl. 2:49–52, 1991]. Interestingly, this is a protein which exhibits immunological cross-reactivity with IL-1 and has been confirmed to suppress the activity of IL-1 by competition with IL-1 on a receptor site. Thereafter, the analysis of the genes encoding the receptor antagonist has demonstrated that it is a distinct protein having a homology of only about 19 to 30% with respect to IL-1.

In recent years, furthermore, a cloned protein having a receptor-like structure has helped the clarification of the presence of ligand by using genetical alterations of the receptor-like protein and the disclosure that the ligand-receptor system regulates the propagation of hematopoetic stem cells. The function of the ligand-receptor system had not been known for long periods of years in the field of hematology. Since the expressed product of c-kit cloned as a cellular oncogene had the structure exhibiting a high degree of homology with respect to the cell surface receptor which had a tyrosine kinase active demain, the cloned c-kit had been estimated to be a receptor that transmits some ligand information in the living body. At a moment when c-kit was cloned, however, the ligand had not been known at all. Under such circumstances, Flanagan, JG. et al. has confirmed the presence of proteins that couple therewith by using genetically modified c-kit proteins. They further have clarified that the proteins having a binding property with c-kit are not expressed in the mouse-derived cells that have been known to genetically possess abnormality in the hematopoietic control system, and have reached a conclusion that they are the hematoblast growth factors and their receptors. The hematopoietic stem cell growth factors and their receptors which have not been known for many years until the disclosure. This discovery is very interesting in that the ligand was identified by using receptors that had been clarified previously.

In view of the fact that the Fas antigen protein of the present invention has the structure that serves as a cell surface receptor, it is clear that various ligands, agonists and antagonists specific or related to Fas antigen, can be developed on the basis of methods or ideas for investigating or reseaching the aforementioned numerous cell surface receptors and a variety of the corresponding molecules against the corresponding receptors such as soluble molecules, ligands and antagonists, or on the basis of methods which are basically the same as or resemble the knowledge obtained therefrom. Therefore, the thus obtained various acting substances such as ligands, agonists and antagonists are or may be encompassed within the scope of the present invention.

The cDNA (e.g. pF58) encoding the Fas antigen of the present invention is inserted into a plasmid for expression under the regulation of a human peptide chain elongation factor 1 $\alpha$ gene promoter to construct an expression plasmid (e.g. pEFF-58). According to the present invention, mouse T cell lymphoma WR19L and mouse fibroblastoma L929 cells are transformed with the above expression plasmid. The flow cytometry analysis of the transformants revealed that the Fas antigen is expressed in very large amounts on their surfaces. It has been further confirmed that the transformed cell lines exhibit a dose-dependent response to the anti-Fas antibody and die. Through the observation of morphological changes, fragmentation of chromosomes and the like, it has been made clear that these cells die due to apoptosis.

The present invention provides DNAs coding for human cell surface antigen Fas and expression vectors for carrying the DNA.

The cDNA (e.g. pP58) encoding the Fas antigen of the present invention can be isolated by ordinary methods from the transformant (e.g. *Esherichia coli*, pF 58 which carries the plasmid pF 58 was originally deposited as a domestic microorganism deposit (FERM P-12192) at the Fermentation Research Institute, Agency of Industrial Science and Technology, Ministry of International Trade and Industry, Japan (FRI) on Apr. 12, 1991 and converted into an international one (PERM BP-3826) under the Budapest Treaty.

The cloning of cDNA coding for the human Fas antigen according to the present invention can be carried out according to conventional methods in the art. The total RNAs are prepared from cells expressing human Fas antigen (e.g. KT-3 cell) and poly(A)RNAs are selected. Then, a double stranded cDNA is synthesized by using reverse transcriptase or the like enzyme and is introduced into a mammal expression vector (e.g. pCEV4 , (Ito et al., 1990) to prepare cDNA libraries. The cDNA libraries (e.g. cDNA libraries of about $8\times10^5$ independent clones) are transfected into mammal cells (e.g. COS-7 cell) by the spheroplast fusion method or the like. After the transfection (e.g. at 72 hr posttransfection), the transfected mammal cells (e.g. the transfected COS-7 cells) are incubated with anti-Fas antibody (e.g. mouse anti-Fas antibody (IgM)), and the mammal cells expressing the Fas antigen (e.g. the COS cell expressing the Fas antigen) are recovered by the panning procedure [Seed and Aruffo, Proc. Natl. Acad. Sci. USA 84, 3365–3369, 1987] using goat anti-mouse IgM or the like.

The extrachromosomal DNA is prepared from the adherent mammal cells (e.g. the adherent COS cells) according to the method of Hirt [J. Biol. Cham. 264, 14929–14934, 1967] or the like, and introduced into *Escherichia coli* or the like. The resultant colonies are pooled, used for spheroplast fusion, etc. with mammal cells (e.g. COS cell), and the panning is performed as described above. This procedure is repeated (e.g. three times) to obtain individual clones (e.g. 14 individual clones (pF1 to pF14)). Then, mammal cells (e.g. COS cells) are transfected with selected clones (e.g. pF1 having 3.0 kb insert and pF3 having 1.5 kb insert) among the individual clones. The resulting cells are analyzed by the flow cytometry using an anti-Fas antibody and the like. In a preferred embodiment of the present invention, it has been found that two cDNAs code for proteins that have the Fas antigen determinant. The pF1 and pF3 have been subjected to the restriction enzyme mapping and the DNA sequencing analysis. As a result, it has been found that the pF1 and pF3 share identical sequences at the 5' end including about 500 bases. However, their sequences at the 3' end diverge completely (see FIG. 3A).

Next, the original cDNA libraries of cells expressing human Fas antigen are screened by the colony hybridization using an isolated DNA fragment derived from cDNA coding for proteins related to the human Fas antigen (e.g. XhoI-BamHI DNA fragment at the 5' end of the pF3). As a result, clones which have full-length DNA encoding Fas antigen are obtained. In a preferred embodiment of the present invention, it has been found that ten clones are isolated and subjected to restriction enzyme mapping. These cDNAs contained inserts of 1.8 to 2.6 kb, showed identical restriction maps and overlapped each other. The longest cDNA clone (pF58) was selected from the resulting clones. FIG. 3 shows the restriction map of the longest cDNA clone (pF58), and FIG. 1 and 2 show the nucleotide sequence and the predicted amino acid sequence.

Figure 3B:
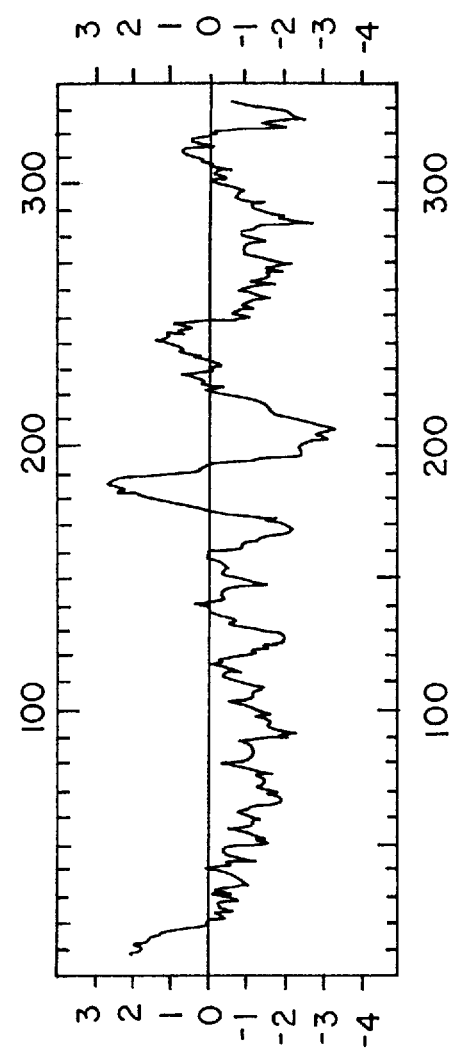
FIG. 3B shows the hydropathy plot of amino acid sequence of human Fas antigen.
Figure 4A:
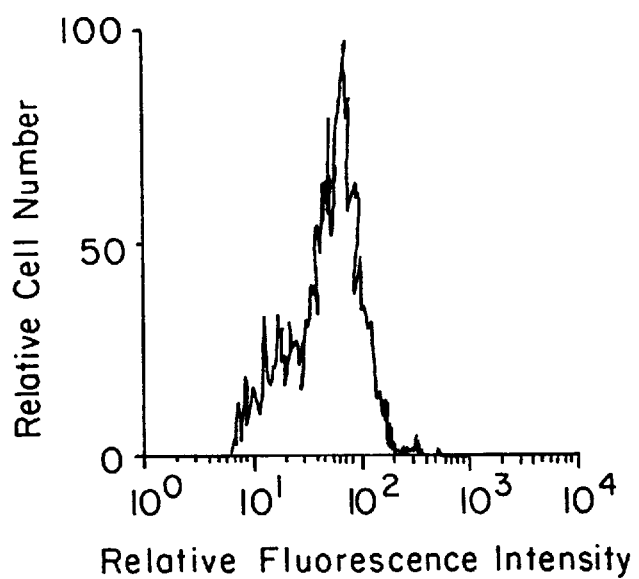
FIGS. 4A–F shows the graph representing the results examined by a flow fluorometry for the expression of the human Fas antigen in mouse cells transformed with the human Fas expression vector. Expression plasmid pEFF-58 and a plasmid carrying the neo-resistance gene were cotransfected into WR19L cells or L929 cells and selection was conducted in the presence of G-418 to give several G-418-resistant clones. Then, parental WR19L and L929 cells, 2 transformants derived from WR19L (58-12a and 58-80d) and 2 clones derived from L929 (LB1 and LB11) were stained with anti-Fas antibody (IgM) and anti-mouse IgM antibody bound with FITC, followed by subjecting to flow cytofluorometry.
Figure 4B:
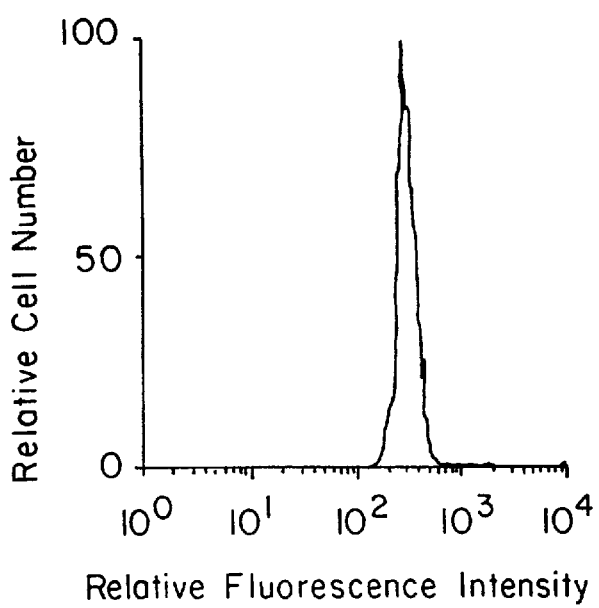
Figure 4C:
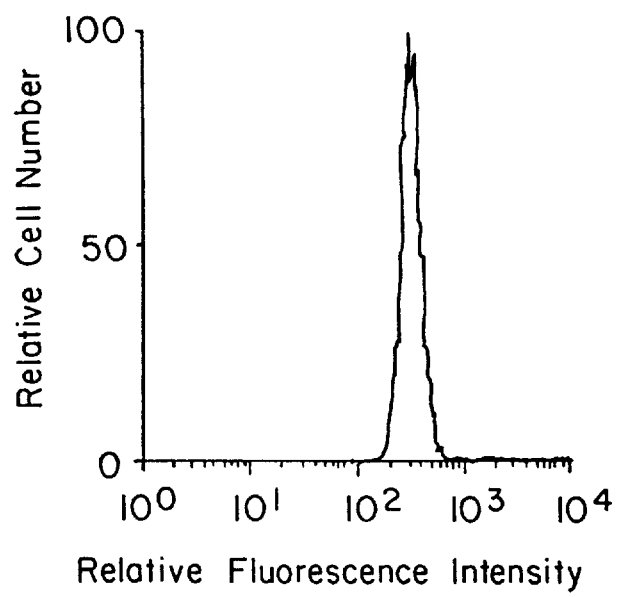
Figure 4D:
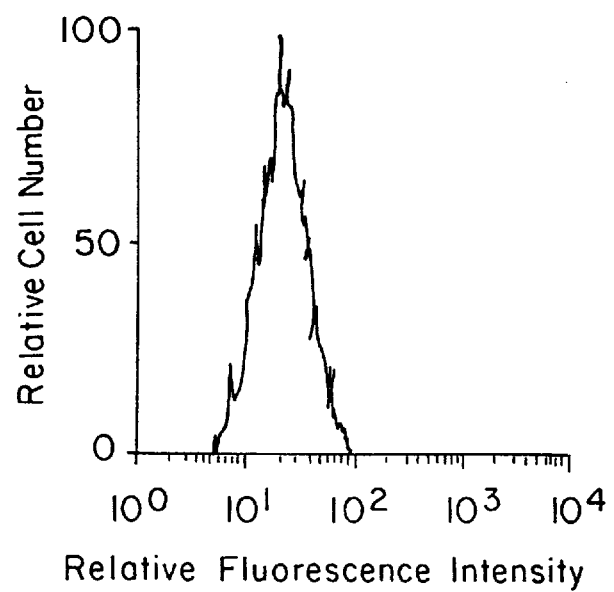
Figure 4E:
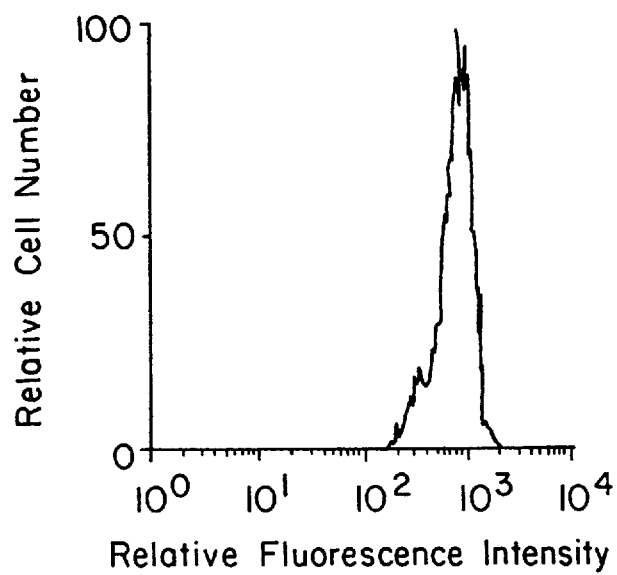
Figure 4F:
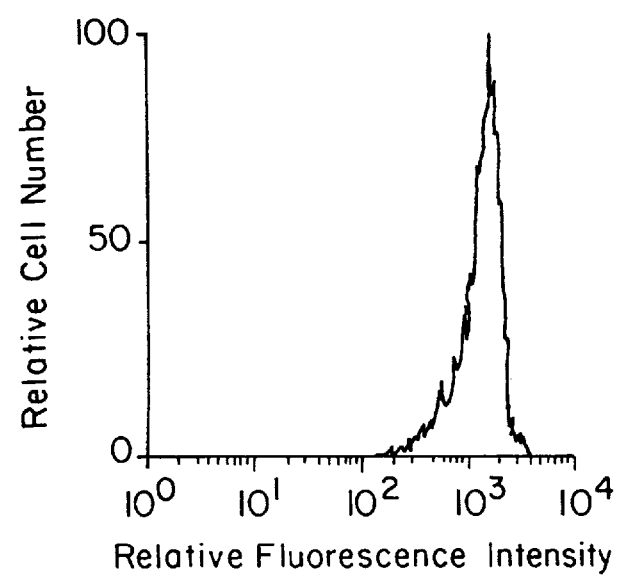

The pF58 cDNA has a long open reading frame of 1008 nucleotides capable of coding for a protein consisting of 335 amino acids. The hydropathy analysis of the predicted amino acid sequence indicates the presence of a signal sequence at the N-terminal end (FIG. 3B). Comparison of the N-terminal sequence with typical signal peptide cleavage sites suggests that the mature Fas antigen would lack the signal peptide portion and be a protein consisting of 319 amino acids having a calculated molecular weight of about 36,000. This Fas antigen protein consists of an extracellular domain of 157 amino acids, a membrane-spanning domain of 17 amino acids, and a cytoplasmic domain of 145 amino acids.

Western blotting analysis of the membrane fractions from KT-3 cells and the WR19L transformant clone, F58-12A, expressing the Fas antigen using the anti-Fas antibody, shows a specific band with an apparent molecular weight of about 43,000. This value is in good agreement with the above calculated value (about 36,000) from the standpoint in which sugar moieties are bonded to two potential N-glycosylation sites found in the extracullular domain of the Fas antigen (see FIG. 1) .

Moreover, the KT-3 cells are subjected to the northern hybridization using the Fas antigen cDNA or its fragment as a probe to detect two bands at 2.7 and 1.9 kb. By taking the presence of the poly(A) tail into consideration, it is considered that the larger mRNA is almost identical to the size of the above pF58 cDNA. It is therefore considered that pF58 is a full-length cDNA for the larger mRNA. If human colon carcinoma HT-29 cells are treated with 300 units/ml human INF-γ for 7 hours prior to harvest, both large and smaller mRNAs for the Fas antigen are expressed distinctly.

Forty percent of the cDNA clones isolated from the KT-3 cDNA libraries by the colony hybridization possessed a length of about 1800 bp. Since the potential poly(A) addition signals can be found at nucleotide position 1831 to 1836 (base Nos. 1831 to 1836) in the 3' noncoding region of pF58 cDNA (FIG. 2), the two different mRNAs for human Fas antigen, found by the northern hybridization, are probably generated by an alternative use of two different poly(A) addition signals.

According to the present invention, the cDNA coding for the human Fas is cloned and the nucleotide sequence is clarified. For people skilled in the art, therefore, it pertains within the scope of the present invention to construct an expression vector capable of expressing a recombinant Fas antigen in a suitable host system. Then, by transforming the host cells with the thus constructed expression vector, the transformed cells are cultured under the conditions suitable for expressing the DNA encoding the Fas antigen in order to prepare a recombinant human Fas antigen. The thus obtained recombinant human Fas antigen is useful in clarifying the apoptosis mechanism of various cells such as immune system cells, and is further effective in preparing monoclonal anti-bodies that spesifically react with tumor cells expressing Fas or of value for the study, research and clinical test of those related to cytolytic activity of TNF.

For instance, the analysis of the cDNA coding for the human Fas antigen as obtained in Example 1 and the analysis of the corresponding encoded amino acid sequences, indicate that the Fas antigen belongs to a group of cell surface receptor proteins.

Here, the proteins thus provided include ones that may be encoded by the DNA of the present invention and may be defined to be the human Fas antigen and the functional homologs thereof. They may be cell surface proteins that are recognized by a monoclonal antibody capable of specifically recognizing the human Fas antigen and that induce apoptosis in the cells with the antibody alone without the presence of any other cytotoxic factor such as complement and the like. Particularly, the present invention provides proteins having the amino acid sequence disclosed in FIGS. 1 and 2 or peptides which are a part of the amino acid sequences thereof.

With the current technical level in this field of science, it will be esay to introduce mutation such as deletions, additions, insertions and/or substitutions to the amino acid sequence without changing fundamental properties (e.g. physical properties, physiological or biological activity, immunological activity, etc.) of the proteins. For instance, substitution of a hydrophobic amino acid residue with other hydrophobic amino acid residue, or of amino acid residue having positive electric charge with other amino acid residue having positive electric charge, mutual substitution among Glu and Asp or Lys, His and Arg, substitution among Ile, Val, Met and Leu groups, substitution among Gly, Ala, Ser and Cys groups, and substitution among Trp, Tyr and Phe groups may be predicted. For easy purification of the proteins of the present invention, furthermore, other proteins such as β-galactositase of *Eschaerichia coli* or mouse IgG Fc fragment may be added to the N-terminal side or/and the C-terminal side of the proteins by the genetic engineering method, or the amino acid sequence may be partly cleaved or substituted by the similar method in order to more deeply analyze the function of the proteins, as can be easily contrived by people skilled in the art. Therefore, such human Fas antigen amino acid mutants are also encompassed by the present invention. For instance, soluble Fas antigens indicated by amino acid Nos.1 to 157 are preferred examples of such mutants.

The nucleotide sequences of cDNAs coding for the human Fas antigen of the present invention are shown in FIGS. 1 and 2. It would be understood that Fas derivatives having substantially the same functions as the natural Fas antigen determinant can be obtained from the above DNAs by inserting, deleting, substituting or cleaving the nucleotides. Therefore, the DNAs thus derived are also encompassed by the scope of the present invention.

The insertion, substitution or deletion of the nucleotides can be carried out by, for example, the site directed mutagenesis, homologous recombination, cleavage with restriction enzymes, or ligation with ligase. The above methods can further be suitably combined with the primer extension using synthetic DNA fragments as primers or the polymelase chain reaction. These methods can be carried out in compliance with the methods disclosed in, for example, Sambrook et al. "Molecular Cloning, A Laboratory Manual, 2nd edition, Cold Spring Harbor Laboratory, 1989, Muramatsu (Ed.) "Labomanual Genetic Engineering" Maruzen Co., 1988, Erlich HE, (Ed.) [PCR Technology, Principle of DNA Amplification and Its Application] Stockton Press, 1989, or in compliance with the modified methods thereof.

In the technical field of genetic engineering, furthermore, it has been known to substitute the bases in the base sequence for other base sequence without changing the amino acid sequence that is encoded thereby. Most of the amino acids are encoded by a plurality of genetic codes. For instance, Val is encoded by any one of GTT, GTA, GTC or GTG and Ala is encoded by any one of GCA, GCT, GCC or GCG. Therefore, the genetic base sequences of the present invention include base sequence substituted mutants that accompany the degeneracy of genetic codes.

From the disclosure of the present invention, furthermore, it would be easy in the art to add a base sequence such as a promoter or an enhancer to the 5' end side in order to produce a large amount of protein encoded by the DNA base sequence, in a transformant, to add a poly A addition signal base sequence to the 3' end side in order to stabilize the mRNA after the transcription, and/or to remove bases from or insert bases in the base sequence of the present invention in order to obtain mutant proteins from which amino acids are partly removed or to which amino acids are partly added in an attempt to further extensively analyze the function of the proteins encoded by the base sequence of the present invention. Therefore, the present invention further encompasses the base sequences having one or more bases that are added, altered, removed or inserted on the 5' end side or on the 3' end side and/or between them in the base sequence of the present invention.

The DNAs of the present invention include DNAs complementary to the DNAs encoding Fas or their fragments, DNAs capable of hybridizing with DNAs which are complementary to the DNAs encoding Fas or their fragments, and DNAs capable of hybridizing with human Fas protein cDNA fragments.

The expression vectors containing DNA coding for the human Fas antigen of the present invention can be constructed by methods known in the art. The vector suitable for expressing human Fas antigen DNA may have a promotor for initiating transcription closely on the upstream side of the DNA inserted site. Suitable promoters have been known in the art and can be selected by depending upon the functional characteristics in the host cells. Examples include a promoter of SV40 virus early gene, promoter of peptide chain elongation factor EF-1α, promoter of metallothioneine gene, promoter of β-actin, and promoter of CMV virus that can be used for the expression in the animal cell systems, as well as a promoter of T7 polymelase and promoter of β-galactositase gene that can be used for the expression in bacteria, particularly *Escherichia coli*, and promoters of phosphoglyceraldehyde dehydrogenase and alcohol dehydrogenease that can be used for the expression in yeasts. It is desired that a termination signal exists at a position downstream of a human Fas DNA inserted site.

In the case of animal cells, such regulators may be those from the human Fas sequence or from other sources of genes. When *Escherichia coli* is used, however, such regulators should desirably be from the *Escherichia coli* gene.

It is desired that the vector comprises a marker for selection such as a drug-resistant marker. A particularly desired example of the marker may include a neomycin-resistant gene, etc. an expression vector containing Fas DNA and a plasmid coding for drug resistance such as an antibiotic may be subjected to the transformation simultaneously.

In order to construct the expression vector, the DNA coding for the human Fas of the present invention is inserted in a suitable vector which can be selected from those already known in the art by taking into consideration of the promoters, termination signal, selection marker and other conditions. Examples of the DNA vector in which the cDNA of the invention is inserted and which is introduced into the host culture cells for expression the cDNA include pKCR, pEF-BOS, CDM8, pCEV4, bovine papilloma virus DNA for expression in the animal cells, pGEMEX, pUC, etc. for expression in *Escherichia coli*, as well as pYG100 YCpAD1, etc. for expression in the yeasts.

Any culture cells may be used for the expression of human Fas antigen of the present invention as long as they are self-replicable and are capable of expressing the DNAs of the present invention. Examples include procaryotic microorganisms such as *Escherichia coli* and eucaryotic microorganisms such as yeasts (Saccharomyces, such as *S.cerevisiae*), as well as tissue culture cell lines derived from eucaryotic living things. Examples of *Escherichia coli* strains suitable for hosts include HB101, DH1, x1776, JM101, and JM109 of which the transformants can be easily sorted depending upon their resistance against drugs and enzymatic activities. Tissue culture cell lines include culture cells drived from insects, birds, mouse, rat, hamster, ape and human. Preferred examples are L cells, 3T3 cells, FM3A cells, CHO cells, COS cells, Vero cells, Hela cells and primary-cultured fibroblasts. Suitable host-vector systems and their use have been known in the art. Among them, any systems can be arbitrarily selected as long as they are suitable for expressing the DNAs of the present invention.

The proteins of the present invention can be produced in such a system by cultivating a host (transformant) under the conditions suitable for the growth and capable of functioning the promoter of vector possessed by the host. These conditions can also be suitably selected and put into practice by people skilled in the art.

The present invention will be described more concretely by the following examples, but they should not be interpreted as limiting the invention in any manner.

In the specification, the technical terms, abbreviations and symbols are those which are conventionally used in the art unless otherwisely stated. Moreover, the processes were conducted by making reference to Sambrook et al. "Molecular Cloning, A Laboratory Manual, 2nd edition", Cold Spring Harbor Laboratory, 1989, Imai Fumio et al., "Introduction of Recombinant Gene into Cells and Expression", Proteins, Nucleic Acids, Enzymes, Special Edition 28 (14), 1983, Yoshio Okada, "Summary of Cellular Engineering Technology", Experimental Medicine, Special Edition 7 (13), 1989, etc.

EXAMPLE 1

Cloning of cDNA Encoding Human Fas (1) Cell and antibody

Human lymphoma cell lines KT-3 ($8\times10^4$, kindly provided by Dr. Shimizu, Kanazawa Medical University) were grown in RPMI 1640 medium supplemented with 10% fetal calf serum (FCS) and 5 ng/ml human recombinant IL-6 (kindly provided by Ajinomoto Co., Inc.). The cell culture (total volume: 2 1) was incubated at 37° C. for 2 days under 5% $CO_2$-95% air.

Mouse T cell lymphoma WR19L cells (ATCC TIB52) (kindly provided by Dr. T. Kinebuchi, Tokyo Institute for Immunopharmacology, Inc.) were grown in RPMI 1640 medium containing 10% FCS.

Monkey COS-7 cells (ATCC CRL1651) and mouse L929 cells were grown in Dulbecco's modified Eagle medium (DMEM) containing 10% FCS.

Mouse anti Fas monoclonal antibody (IgM) was prepared in the same manner as mentioned above [Yonehara et al. (1989) op. cit.] and purified by column chromatography on hydroxyapatite.

(2) Construction of cDNA Library

Total RNA (2.7 mg) was prepared from the KT-3 cells ($1.2\times10^9$), by the guanidium isothiocyanate/acid phenol method [Chomczynski and Sacchi, Anal. Biochem.,162, 156–159 (1987)] and poly(A)RNA (137 µg) was selected by means of an oligo(dT)-cellulose column chromatography. The poly(A)RNA (5 µg) was employed in synthesis of cDNA. Double strand cDNA primed with random hexamer oligonucleotide ($pdN_6$) or oligo(dT) was synthesized in the same manner as described in the report [Fukunaga et al., Cell, 61: 341–350 (1990)] except that M-MLV RNaseH— reverse transcriptase was employed instead of the AMV reverse transcriptase.

After addition of BstXI non-palindromic adapter (2 µg), DNA ligase (350 units), and ATP (final concentration: 1.0 mM), the mixture was reacted at 4° C. for 18 hours to ligate the adaptors to both ends of the synthesized double stranded DNA. The cDNA larger than 2 kb was recovered from the agarose gel and 0.25 µg of the recovered cDNA was ligated to BstXI-digested mammalian expression vector pCEV4 (0.2 µg) [Itoh et al., Science, 247, 324–327 (1990)] to construct the cDNA library. E. coli VM1100 cells were transformed with the cDNA by the electroporation method [Dower et al., Nucleic Acids Res., 16, 6127–6145 (1988)]. The individual clones of about $4.3\times10^5$ from the oligo(dT)-primed cDNA library were mixed with the clones of about $4.0\times10^5$ from the randam hexamer-primed cDNA library and transfection with COS-7 cells was carried out as described below to recover the cDNA clones.

(3) Recovery of cDNA by Panning

The panning plates (panning dishes) were prepared as described below.

The bacterial 6 cm dishes (plates) (Falcon 1007) were incubated at room temperature for 90 minutes with 3 ml of 50 mM Tris-HCl (pH 9.5) containing 10 µg/ml goat anti-mouse IgM (Cappel). The plates were washed three times with 0.15M NaCl and then incubated at room temperature overnight with 3 ml of phosphate-buffered saline (PBS).

One hundred and eight 6 cm dishes each containing 50% confluent monkey COS-7 cells (ATCC CRL1651), which were incubated in Dulbecco's modified Eagle medium containing 10% FCS, were transfected by the spheroplast fusion method [Sandri-Goldrin et al., Mol. Cell. Biol., 1, 743–752 (1981)] using the KT3 cDNA library comprising about $8\times10^5$ individual clones as described above.

After 72 hours from the transfection, the cells were detached from the dishes by incubation in PBS containing 0.5 mM EDTA and 0.02% $NaN_3$ (PBS/EDTA/$NaN_3$) at 37° C. for 30 minutes. The detached cells were pooled, collected by centrifugation and then suspended in 9 ml of cold PBS/EDTA/$NaN_3$ containing 10 µg/ml anti-Fas antibody. After incubation on ice for 60 minutes, the cells were diluted with an equal amount of PBS/EDTA/$NaN_3$ and centrifuged at 1000 rpm for 5 minutes through PBS/EDTA/$NaN_3$ containing 2% Ficoll 400. The pelleted cells were resuspended in 27 ml of PBS/EDTA/$NaN_3$ supplemented with 5% FCS and filtrated through Nylon meshes (pore size of 100 µm) to remove the aggregates. Then, the cells were distributed into 54 panning plates, each containing 5 ml of. PBS/EDTA/$NaN_3$ and 5% FCS. After incubation at room temperature for 2 to 3 hours, the Fas-expressing cells were adhered onto the plates and then nonadhering cells were removed by gently washing three times with 2 ml of PBS/EDTA/$NaN_3$ containing 5% FCS. Then, the extrachromosoval DNA was prepared from the adhered COS cells according to the Hirt method [(1967), op. cit.]. More specifically, into each plate was placed 0.4 ml of 0.6% SDS solution containing 10 mM EDTA and each plate was incubated at room temperature for 20 minutes. The lysates were collected into microfuge tubes, NaCl was added up to 1M and the tubes were placed on ice for at least 5 hours. After centrifuged at 13,000 rpm, for 5 minutes, the supernatants were extracted with phenol/chloroform and the DNA was recovered by ethanol precipitation. With the DNA recovered from the first round of panning was transformed Escherichia coli VM1100 to give about $3.2\times10^5$ colonies. They were subjected to sphereplast fusion with COS cells in 48 plates, each being of 6 cm. Panning was performed with 24 plates in the same manner as described above and the DNA was prepared from the adhered cells. The so recovered DNA was transformed to give about 10,000 colonies, which were used for the third cycle of the spheroplast fusion with COS cells (24 plates, each being of 6 cm) and panning was performed in 12 plates, each being of 6 cm, to prepare the DNA from the adhered cells.

Transformation of E. coli VM1OO was performed with the DNA finally obtained by the said three procedures and, among $2.8\times10^5$ clones, 14 of the resultant clones (pF1–pF14) were analyzed.

By digestion of the 14 plasmid DNA's with restriction enzyme, it has been elucidated that one group has the same insert of 3.0 kb (pF1, 2, 5, 11), while another group has the same insert of 1.5 kb (pF3, 4, 6, 7, 9).

By using the pF1 and pF3 among them, COS cells were subjected to transfection and the cells were analyzed by a flow cytometry using anti-Fas antigen to confirm the two cDNAs code for Fas antigen determinant.

The restriction mapping and DNA sequence analysis of pF1 and pF3 showed that they share identical sequences at the 5' end up to 0.57 kb, but their sequences at the 3' end diverge completely.

Then, the cDNA libraries of the above-mentioned KT-3 cells were screened by colony hybridization using the XhoI-BamHI DNA fragment (about 520 bp) as the 5' end of pF3. Ten colonies were obtained from $2 \times 10^5$ clones, said 10 clones showing identical restriction maps and overlapped each other. The longest cDNA clone was selected and designated pF58. Schematic representations and restriction maps of the pF58 and the said pF1 and pF3 are shown in FIG. 3A. In the FIG. 3A, the open box represents the open reading frame, the hatched box represents the signal sequence, and the black box represents the transmembrane region, respectively. In the representations for pF1 and pF3, the solid lines show identical sequence to that of pF58, while the dotted lines show difference sequence from that of pF58. However, the pF3 cDNA contains a single base (T) deletion at the position indicated with an arrowhead, the point of which is different from the pF58 cDNA.

FIG. 3B shows a hydropathy plot of human Fas antigen, which was obtained by the method of Kite and Doolittle [J. Mol. Biol., 157, 105–132 (1982)]. The numbers under the plot show positions of the amino acid residues of the precursor protein.

Then, the nucleotide sequence of the clone pF58 and its predicted amino acid sequence were determined. The results are shown in FIG. 1 and FIG. 2, which are identified in the Sequence Listing as SEQ ID NO:1 and SEQ ID NO:2.

The cDNA analysis has elucidated the following points:

(1) The cDNA consists of 2534 bp and has a poly(A) addition signal (ATTAAA) at the 3'-end.

(2) There is a long open reading frame (1,008 nucleotides). The open reading frame can code for a protein consisting of 335 amino acids, starting from the initiation codon at the nucleotide positions 195 to 197 and ending at the termination codon TAG at the positions 1200 to 1202.

The results of the hydropathy analysis of the amino acid sequence suggested the presence of a signal sequence at the N-terminal end (See, FIG. 3B). Comparison with typical signal peptide cleavage sites suggested that the mature protein start at the 17th amino acid (Arg).

Therefore, the mature Fas antigen is a protein consisting of 319 amino acids with a calculated molecular weight of 36,000 and has the transmembrane segment consisting of 17 uncharged amino acids from Leu-154 to Val-170. And, it is followed by 3 basic amino acids at the cytoplasmic domain, as observed in other membrane-spanning proteins.

It has been indicated from the above results that this protein consists of an extracellular domain of 157 amino acids, a membrane-spanning domain of 17 amino acids and a cytoplasmic domain of 145 amino acids and that the extracellular domain is rich in cystein residue (18 residues in 153 amino acids) and the cytoplasmic domain is relatively abundant in charged amino acids (24 basic amino acids and 19 acidic amino acids in 143 amino acids).

In FIG. 1 and FIG. 2 showing the nucleotide sequence and amino acid sequence of the Fas protein, the numbers above and below each line refer to the nucleotide position and the amino acid position, respectively. Amino acid numbers start at Arg-1 of the mature Fas protein. The transmembrane domain is underlined and two potential N-linked glycosylation sites (Asn-X-Ser/Thr) are indicated by asterisks. Three poly(A) addition signals (ATTAAA) are indicated as overlined. The nucleotide deleted in the pF3 is indicated with an arrowhead.

(3) Comparison in sequences of the Fas antigen with other members of the NGFR/TNFR family.

Figure 9:
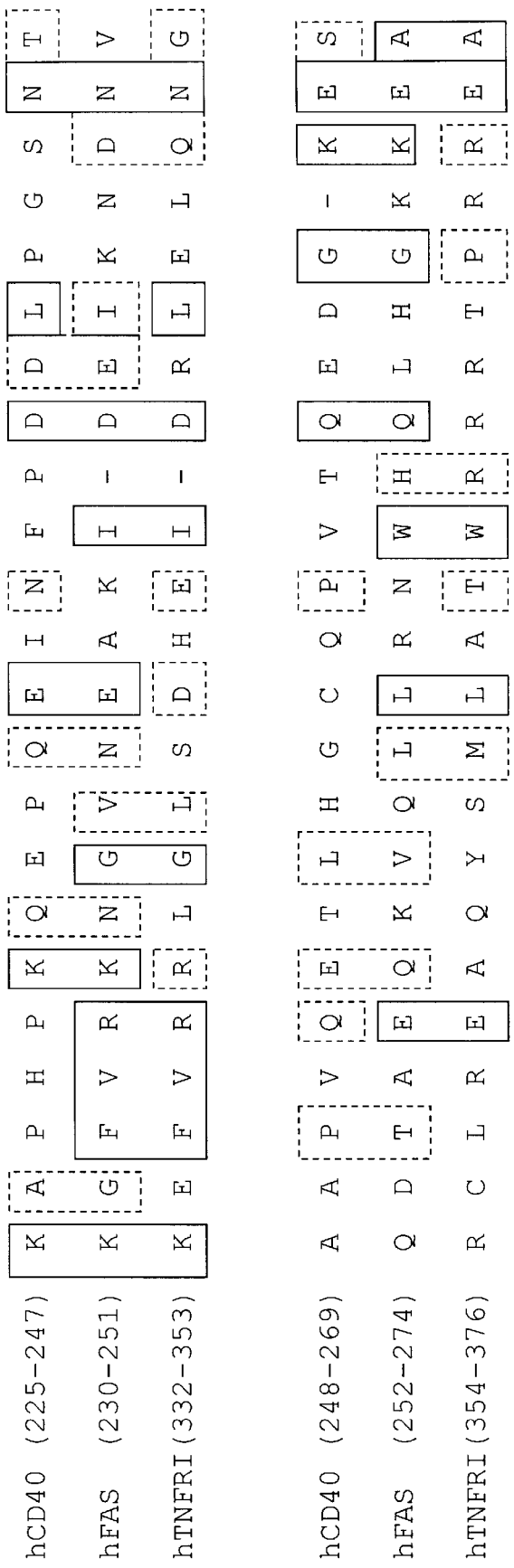
FIG. 9 shows the comparative representation of the amino acid sequences of the cytoplasmic domains of the Fas, TNF receptor type I and CD40 (see SEQ ID NOS: 9–11).

Comparison of the amino acid seqeunce of the Fas antigen with the sequences of other members of the NGFR/TNFR family was performed. The results are shown in FIGS. 7–9.

Figure 7:
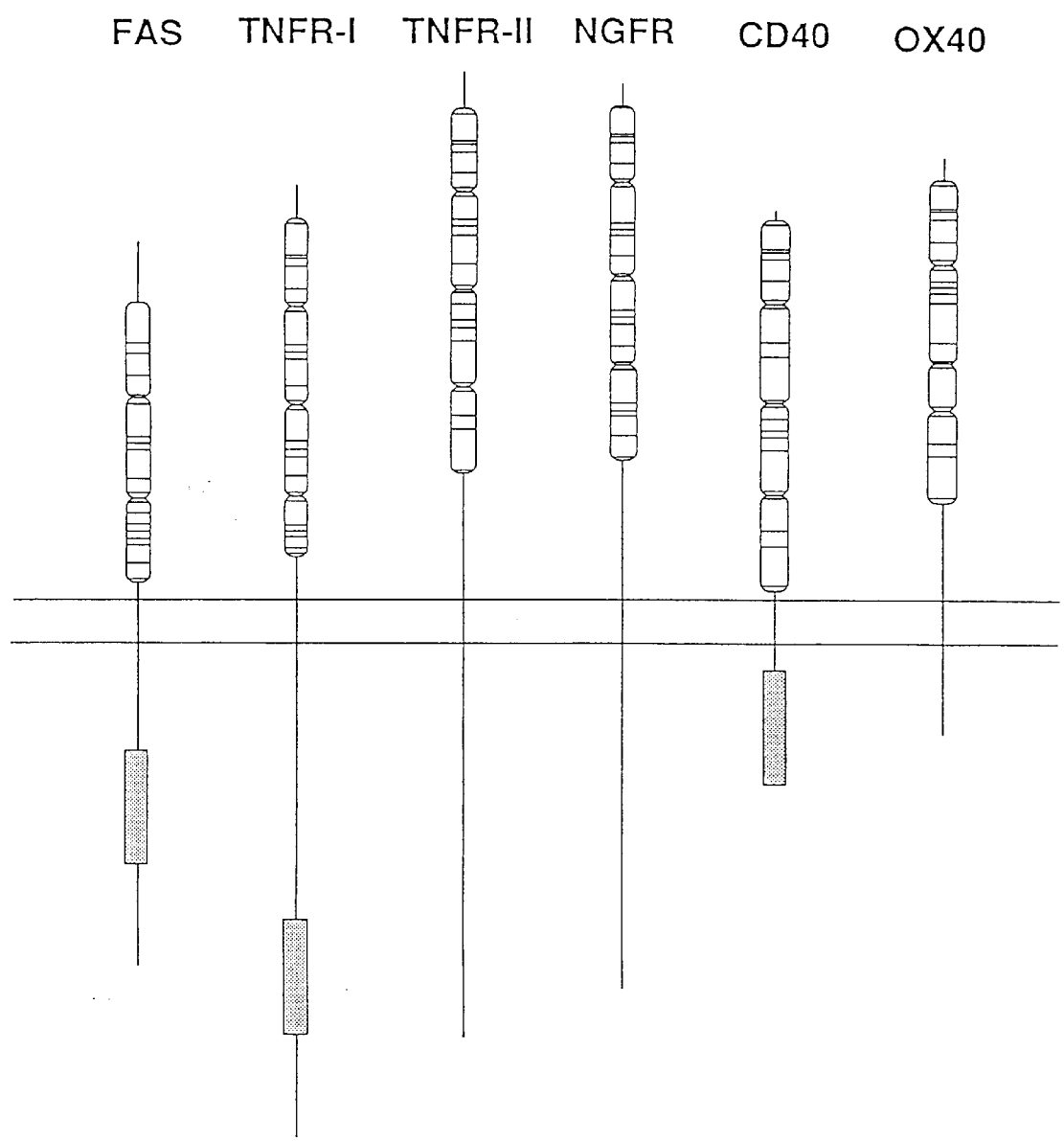
FIG. 7 shows the schematic representation of comparison in amino acid sequence of Fas antigen with other members of the NGFR/TNFR family.

FIG. 7 is a schematic representation of the cysteine-rich repeats of the extracellular domain. In open boxes, the cysteines are represented with bars, and the stripped boxes in the cytoplasmic domain represent the conserved region among the Fas antigen, the TNF receptor type I and the CD40 antigen. It has been indicated from this Fig. that the extracellular domains of the TNF receptor, the NGF receptor and the CD40 antigen can be divided into 4 cysteine-rich subdomains, while the Fas antigen and the CD40 antigen contain 3 subdomains.

Figure 8B:
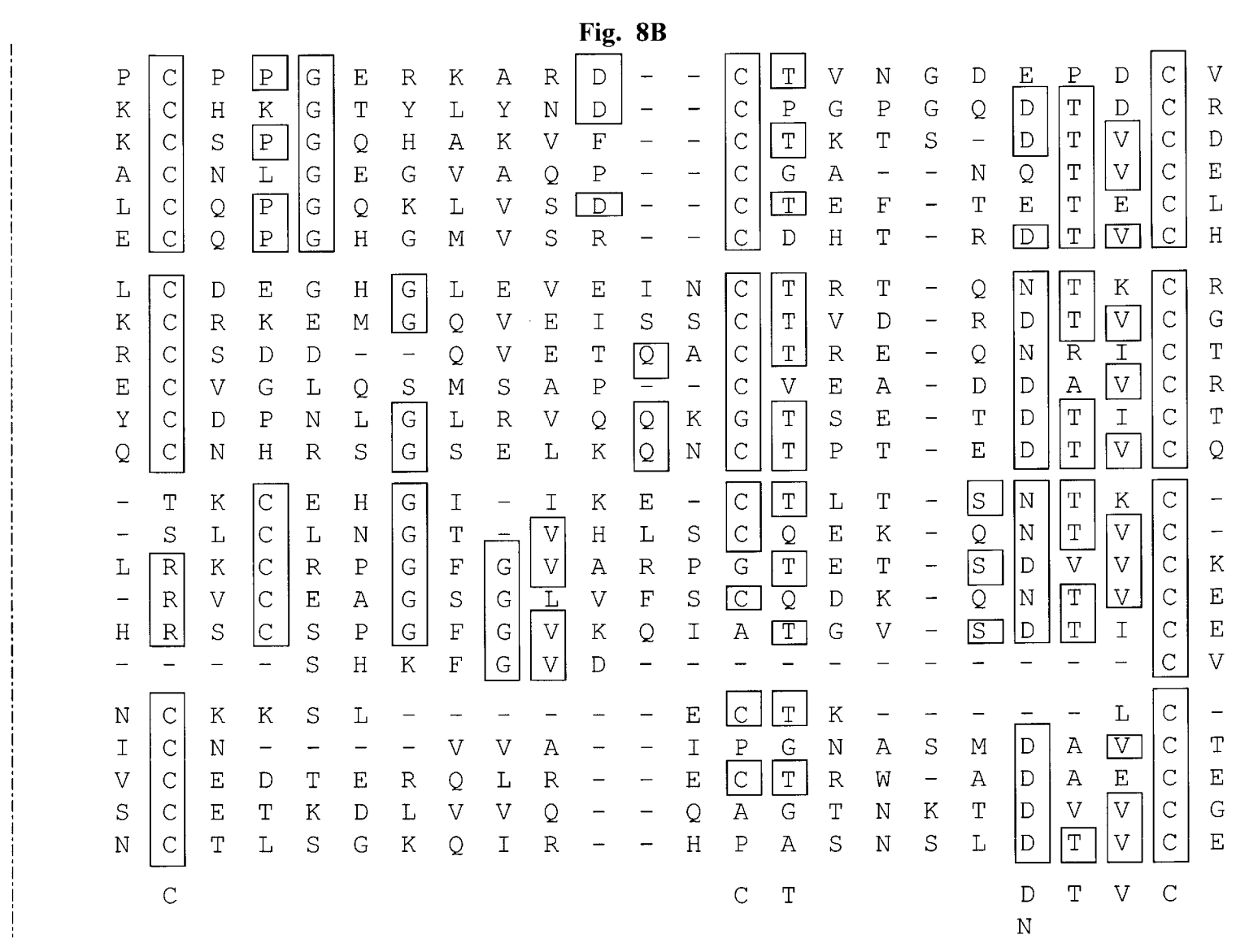

FIG. 8 shows the amino acid sequences of the extracellular domains of human Fas (hFas), human TNF receptor type I (hTNFR1) (Schall et al., 1990), human TNF receptor type II (hTNFR2) [Smith et al., Cell, 61, 361–370 (1990)], human NGF receptor (hNGFR) [Johnson et al., Science, 248, 1019–1023 (1986)], human CD40 (hCD40) [Stamenkovic et al., EMBOJ., 8, 1403–1410 (1989)] and rat OX40 (rOX40) [Mallett et al., EMBO J.,9, 1063–1068 (1990)] which are identified in the Sequence Listing as SEQ ID NO: 3, SEQ ID NO: 4, SEQ ID NO: 5, SEQ ID NO: 6, SEQ ID NO: 7, and SEQ ID NO: 8. Gaps(-) are introduced to optimize matches. Identical amino acids are boxed.

It has been indicated from this Fig. that the positions of the cysteine residues are well conserved. The numbers referring to residues are followed as in references. The amino acid residues conserved among the cysteine-rich repeating units are indicated at the bottom of the sequence. FIG. 9 is a comparison representation of the cytoplasmic domains of the Fas, the TNP receptor I and the CD40 which are identified in the Sequence Listing as SEQ ID NO: 9, SEQ ID NO: 10, and SEQ ID NO: 11. The amino acid sequences of the corresponding regions of the hCD 40, hFas and hTNFR1 are aligned. Identical and conserved amino acids are boxed in solid and dotted lines, respectively.

It has been established that the Fas of this invention belong to the group of such cell surfase proteins.

EXAMPLE 2

Preparation of Transformants Expressing Fas Antigen

The 2.6 kb XhoI fragment containing the Fas cDNA was prepared from the plasmid pF58 (2 µg) and transfected into the BstXI site of a mammalian expression plasmid pEF-BOS [Mizushima and Nagata, Nucleic Acids Res.,18, 5322 (1990)] using a BstXI adapter to construct the expression vector pEFF58 containing the Fas-coding cDNA under the control of human peptide chain-elongation factor 1α gene.

(1) Transformation of mouse fibroblastoma L929 cells was performed according to the following method:

L929 cells $1 \times 10^6$, which were grown in DMEM containing 10% FCS, were cotransfected with 0.2 µg of pSTneoB containing neomycin-resistant genes and 20µg of ApaL1-digested pEFF58 in a 10 cm plate by the calcium phosphate coprecipitation method [Sambrook et al. "Molecular Cloning, A Laboratory Manual, 2nd edition", Cold Spring Harbor Laboratory, 1989], followed by treatment with glycerol. After 12 hours from the transfection, the cells were treated with trypsin, diluted ten times and neomycin-resistant cells were selected in a medium containing 0.4 mg/ml G-418.

After sufficient growth, the cells were washed with PBS/EDTA/NaN$_3$ containing 5% FCS and incubated for 60 minutes on ice in the same buffer containing 10 µg/ml mouse anti-Fas antigen. The expression of the Fas antigen in the transformants was examined by the following processes:

The cells were washed to remove the unbound anti-Fas antibody and then stained for 30 minutes on ice with 10

μg/ml FITC-conjugated goat anti-mouse IgM (Cappel). The cells were centrifuged at 1,000 rpm for 5 minutes through a cushion of PBS/EDTA/NaN$_3$ containing 2% Ficoll, and analyzed on a FACSCAN a flow cytemeter (Becton Dickson Instruments, USA).

(2) Transformation of mouse T-cell lymphoma WR19L cells was performed by the following method:

WR19L cells (1×10$^7$ in 0.8 ml, ATCC TIB52, kindly provided by Dr. T. Kinebuchi, Tokyo Institute for Immunopharmacology, Inc.), which were grown in RPMI1640 containing 10% FCS, were cotransfected with 2.5 μg/ml EcoRI-digested pHAMneo (Clontech) and 25 μg/ml VspI-digested pEFF58 by electroporation [Potter et al., Proc. Natl. Acad. Sci. USA, 81, 7161–7165 (1984)] [at 290V, with a capacitance of 950 μF; Gene Pulser (Bio-Rad)]. The cells were cultured in a growth medium in 96-well microtiter plates (0.1 ml/well) for 2 days and neomycin-resistant clones were selected in a medium containing G-418 at a final concentration of 900 μg/ml. After 9 days, the expression of the Fas antigen in individual G-418-resistant transformants was analyzed on a flow cytofluorometer by mouse anti-Fas antibody and the Fas-positive cells were cloned by a limiting dilution method. Then, the WR19L transformant clone, F58-12a, expressing the Fas antigen was analyzed by a Western Blotting method.

(3) Western Blotting of F58-12a

Membrane fractions from the mouse WR12L cell line, its transformant clone expressing the Fas antigen (58-12a) and human KT-3 were analyzed by Western Blotting with anti-Fas antibody on control IgM. The results showed a specific band with an apparent molecular weight of 43,000. This value is in good agreement with that calculated from the Fas antigen amino acid sequence, in considering the difference wherein the sugar moieties may be attached to the two potential N-glycosylation sites on the extracellular domain of the Fas antigen as shown in FIG. 2.

EXPERIMENTAL EXAMPLE 1

Cytolytic Activity of Anti-Fas Antibody on Fas-Expressing Cells

As described hereinabove, mouse anti-Fas monoclonal antibody showed a cytolytic effect on human cells (U-937, HL-60, A637 or FL cells), but the antibody does not react with mouse cells [Yonehara et al., op. cit.].

In this Example, it was examined whether the polypeptide coded by the present pF58 cDNA may mediate the cytolytic activity of anti-Fas antibody. Mouse WR19L and mouse L929 were transformed as described in Example 2 to prepare transformant cells expressing Fas antigen. These cells are different in the point wherein L929 cells can be killed by TNF in the presence of actinomycin D, while WR19L cells are susceptible to the cytolytic activity of TNF in the presence or absence of any metabolic inhibitors.

As described hereinabove, the expression plasmid pEFF-58 and a plasmid carrying the neo-resistance gene were cotransfected into WR19L cells or L929 cells and selection in the presence of G-418 afforded several G-418-resistant clones.

Then, parental WR19L and L929 cells, 2 transformants derived from WR19L (58-12a and 58-80d) and 2 clones derived from L929 (LB1 and LB11) were stained with anti-Fas antibody (IgM) and anti-mouse IgM antibody bound with FITC, followed by subjecting to flow cytofluorometry.

The results are shown in FIG. 4, wherein A: WR19L; B:58-12a; C: 58-80d; D: L929; E: LB1; F: LB11.

As apparent from the FIG. 4, the parental cells, mouse WR19L and L929 cells, did not express the Fas antigen, while the WR19L transformant cells (58-12a, F58-80d) and L929 cells (LB1 and LB11) extremely abundantly expressed the Fas antigen on their surfaces.

Then, the cytolytic effect of the Fas antibody was examined using the Fas antigen-expressing cells.

Figure 5:
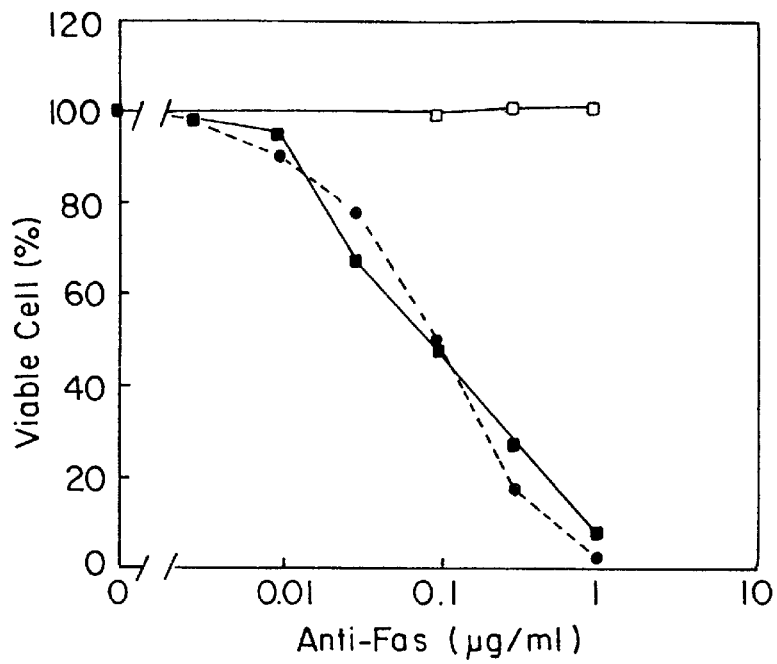
FIG. 5 shows the graph representing cytolytic effect of the anti-Fas antibody on the WR19L transformant clones.

The mouse WR19L cell and its transformant clones (58-12a and 58-80d) were incubated with various concentrations of anti-Fas antibody (0~1 μg/ml) at 37° C. for 24 hours. Viable and dead cell counts were determined by the trypan blue exclusion method. The results are shown in FIG. 5, wherein open squares represent WR19L, closed circles represent 58-12a and closed squares represent 58-80d. As apparent from the FIG. 5, the F58-12a and F58-80d cell lines responded to the anti-Fas antibody in a concentration-dependent manner. The half-maximal response was obtained at 0.1 μg/ml concentration of the anti-Fas antibody and the cells were completely killed by incubation for 24 hours in the presence of 1μg/ml said antibody.

The cytolytic effect of the anti-Fas antibody on the L929 transformant clones was examined according to the following method.

The L929 cells and the transformant clones expressing recombinant human Fas antigen (LB1 and LB11) were dispersed onto 96-well microtiter plates (25,000 cells/well) and incubated for 24 hours. Actinomycin D was added at a final concentration of 0.5 μg/ml and the cells were incubated with various concentrations of anti-Fas antibody (30 ng~2 μg/ml) at 37° C. for 17 hours. Then, the cells were stained with a solution of 0.75% crystal violet in 50% ethanol, 0.25% NaCl and 1.75% formaldehyde at room temperature for 20 minutes. Dye uptake was assessed by the OD value measured at 540 nm using Micro-ELISA autoreader, as expressed as a percentage of the OD measured value without anti-Fas antibody. The results are shown in FIG. 6, wherein open squares represent L929, closed circles represent LB1 and closured squares represent LB11.

Figure 6:
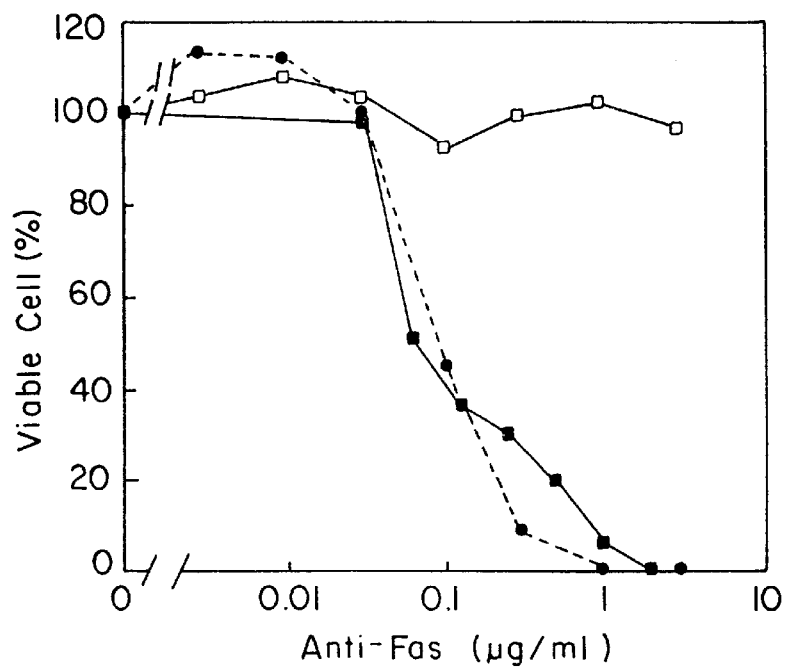
FIG. 6 shows the graph representing cytolytic effect of the anti-Fas antibody on the L929 transformant clones.

As apparent from the FIG. 6, the LB11 and LB1 cell lines responded to the anti-Fas antibody in the presence of actinomycin D in a similar concentration-dependent manner to that of the WR19L cells expressing Fas.

In any causes, the parental mouse WR19L and L929 were not affected by the anti-Fas antibody at a concentration of 1 μg/ml under the same conditions.

EXPERIMENTAL EXAMPLE 2

Apoptosis Induced by Anti-Fas Antibody

Apoptosis of cells induced by Fas was proved according to the following method:

(1) Fragmentation of Chromosomal DNA

The WR19L cell and its transformant clones, 58-12a and 58-80d cells, were incubated in the presence of 300 ng/ml anti-Fas antibody or 60 ng/ml mouse TNF-α. Before incubation and after 1 hour, 2 hours and 3 hours incubation, total DNA was prepared from cells and analyzed by 2% agarose gel electrophresis in the presence of 0.5 ug/ml ethidium bromide. The fragmentation of chromosonal DNA was observed. The fragmented DNA was separated in a laddered pattern and its minimum size was approximately 180 bp. This laddered DNA fragments were observed within 1 hour of incubation and more than 60% of chromosonal DNA was fragmented after 3 hours of incubation. On the other hand, the chromosomal DNA from the parental WR19L cells remained as a high molecular weight form even after incubation with the anti-Fas antibody.

A similar DNA fragmentation was observed in the parental WR19L cells and their transformant cells treated with 60 ng/ml TNF. This was similarly observed in L929 cells.

These results suggest that the specific binding of the Fas antibody to the Fas antigen on the cell surface induces an endonuclease which digests the chromosonal DNA. They are consistent with those properties of apoptosis observed in various systems [Schmid et al., (1987); Ucker, (1987); Smith et al., (1989); Williams et al, (1990), op. cit.]. And, the expression of the Fas antigen in mouse WR19L and L929 cells does not affect a cell-killing effect of TNF and the transformant cells were also killed with mouse TNF-A at the same concentration as in parental cells.

(2) Morphological changes

Morphological changes in the L929 transformant expressing the Fas antigen were examined.

Morphological changes of the LB1 cells were initiated after incubation in the presence of 0.5 μg/ml actinomycin D and in the presence of 1 μg/ml anti-Fas antibody for 3 hours and, after 5 hours, many typical apoptosic blebs were seen on cell surface. Then, almost all cells were detached from plates within 24 hours. Such morphological changes of the LB1 cells were not observed even in the presence of actinomycin D unless the Fas antibody was present. And, the anti-Fas antibody did not give any morphological changes to parental L929 cells.

It becomes apparent, as described in the above Experimental Example, that the human Fas antigen obtained in this invention can mediate apoptosis of cells. Recombinant human Fas can be prepared using the present cDNA by a recombinant DNA technology. Further, the monoclonal antibody to specifically act the human Fas can be also prepared readily in a well-known manner. Thus, these are provided diagnostic and therapeutic means for diseases and disorders in which the cells expressing the Fas antigen would participate.

According to the disclosure related to DNA coding for the human Fas antigen, proteins encoded by the DNA, amino acid sequences thereof and methods for treating and identifying them of the present invention, it becomes possible to apply them to the below-mentioned fields of basic studies and the fields applied industries. The present invention encompasses those that are thus obtained.

At least a part of the DNAs of the present invention may be adopted to variations in order to study the kinds and amounts of expression tissues of the corresponding mRNAs. The results may serve as data which are very useful in estimating the functions of the coded proteins in vivo. At least a part of the base sequences may be adopted to variations in order to isolate Fas antigen genome DNAs. These results may offer data that are of value for analyzing the structure of the Fas antigen genes and for estimating the mechanism of expression control.

Moreover, the sequence of the present invention can be used in studying the polymorphism of Fas antigen genes, enabling the correlation between the genetic diseases and Fas to be closely studied. It is of course allowable to use the DNAs of the present invention as probes for isolating the genes that correspond to Fas antigens of experimented animal species other than human.

In recent years, so-called transgenic animal technology has been put into practice to create an animal in which expression of particular genes are artificially reinforced or suppressed by triggering genetic homologous recombination phenomenon to the gametes or generated early embryo of a higher animal, and the DNA of the present invention can be applied to even such technologies. It is estimated that a species of an experimented animal, in which expression of a Fas gene is reinforced or suppressed, may serve as a new model animal of diseases. It is further possible to study correlation between the Fas antigen genes or Fas antigens and the diseases using these animals, as well as to develop novel therapeutic agents for medical treatment.

The DNAs of the present invention make it possible to produce human Fas antigens in large amounts based on the genetic engineering method. The thus produced Fas antigens are not only useful in the analysis of the functions but can further be used in preparing antisera and monoclonal antibodies. The antiserum and the monoclonal antibody are useful in analyzing the distribution or dinamics of Fas antigens in the blood or tissues, and, hence, the study of correlation relative to various diseases will enable the immunological diagnosis to be carried out.

By using Fas antigens produced in large amounts, furthermore, it is allowed to clone genes coding for proteins that bind to Fas. The cDNAs coding for proteins that bind to Fas may be cloned and selected from expression libraries of various tissues such as placenta by utilizing the reactivity with human Fas antigen as an indicator. In this case, it is allowed to use a soluble Fas antigen lacking a membrane-spanning region or a modified Fas antigen linked with a genetic product encoded by other genes that may serve as markers. The cDNA thus obtained may be applied to the recombinant DNA technology which makes it possible to express a protein capable of reacting with the Fas antigen. Moreover, the human Fas antigen may be bound to a carrier (including a resin) such as SEPHAROSE (a protein A-coupled affinity chromatography gel) activated with cyanogen bromide to prepare an affinity column. For example, human sera, urea or tissue extracts may be chromatographed on the affinity column to obtain proteins capable of reacting with the Fas antigen. It is further possible to clone the cDNAs utilizing the amino acid sequence of purified proteins. For instance, it may be possible to synthesize a primer for PCR, to extract an RNA from various tissues such as thymus or bone marrow lymphocytes, and to clone cDNA by the reverse PCR method.

Furthermore, the soluble Fas antigen lacking a transmembrane region would compete with the Fas antigen on the cell membrane in vivo to suppress its Fas activity. Therefore, such Fas antigen mutants may be applied as medical drugs.

It is estimated that what binds to the Fas antigens is not limited to the proteins mentioned above. Therefore, the Fas antigens of the present invention may be used in searching natural or artificially synthesized molecules capable of reacting therewith.

The substances obtained by the above research may be used as agonists or antagonists against the Fas antigens and offer data that are useful in developing new medical drugs. Furthermore, they may be useful in searching agonists and antagonists capable of working upon the signal transduction mechanism through the studies of the transmission mechanism of secondary and tertially stimulation signals from the of cells into the cells throuh Fas antigen.

Since the apoptosis is found in the extinction process of self-component reactive T cells, it is expected that the Fas antigen may be closely related to autoimmune diseases such as articular rheumatism and SLE, and the above-mentioned agonists and antagonists may serve as therapeutic drugs for such diseases.

It goes without saying that the amino acid mutant proteins of the present invention may be of value in the same fashion as mentioned above.

5,874,546

What is claimed is:

1. A purified Fas antigen consisting of the amino acid sequence from amino acid No. −16 to 319 of that shown in FIGS. 1 and 2, and in SEQ ID NO: 2.

2. A purified Fas antigen consisting of the amino acid sequence from amino acid No. 1 to 319 of that shown in FIGS. 1 and 2, and in SEQ ID NO: 2.

3. A Fas antigen extracellular domain consisting of the amino acid sequence from amino acid No. −16 to 157 of that shown in FIGS. 1 and 2, and in SEQ ID NO: 2.

4. A Fas antigen extracellular domain consisting of the amino acid sequence from amino acid No. 1 to 157 of that shown in FIGS. 1 and 2, and in SEQ ID NO: 2.

5. A Fas antigen fragment consisting of the amino acid sequence from amino acid No. −16 to 174 of that shown in FIGS. 1 and 2, and SEQ ID NO: 2.

6. A Fas antigen fragment consisting of the amino acid sequence from amino acid No. 1 to 174 of that shown in FIGS. 1 and 2, and SEQ ID NO: 2.

7. The Fas antigen of any one of claims 1–6 which is a recombinant protein.

8. A composition comprising at least one of the Fas antigen of any one of claims 1–6, and a physiologically acceptable carrier or diluent therefor.

9. A composition comprising the Fas antigen of claim 7, and a physiologically acceptable carrier therefor.

* * * * *